US011079401B2

(12) United States Patent
Wright et al.

(10) Patent No.: US 11,079,401 B2
(45) Date of Patent: Aug. 3, 2021

(54) APPARATUS AND METHOD FOR INDICATING AT LEAST ONE PROPERTY RELATED TO AN OBJECT

(71) Applicant: 9106634 CANADA LTD., Peterborough (CA)

(72) Inventors: Stephen James Wright, Peterborough (CA); Alexander Michael Bushell, Fraserville (CA); Christopher Joseph Sanders, Peterborough (CA); Pedro Goncalo Ferreira, Peterborough (CA); Robert Maxwell Sheward, Peterborough (CA); Erik Frederik Gerardus Lammers, Peterborough (CA)

(73) Assignee: 9106634 CANADA LTD., Peterborough (CA)

( * ) Notice: Subject to any disclaimer, the term of this patent is extended or adjusted under 35 U.S.C. 154(b) by 165 days.

(21) Appl. No.: 16/083,019

(22) PCT Filed: Mar. 9, 2017

(86) PCT No.: PCT/CA2017/050314
§ 371 (c)(1),
(2) Date: Sep. 7, 2018

(87) PCT Pub. No.: WO2017/152285
PCT Pub. Date: Sep. 14, 2017

(65) Prior Publication Data
US 2019/0234979 A1    Aug. 1, 2019

Related U.S. Application Data
(60) Provisional application No. 62/305,572, filed on Mar. 9, 2016.

(51) Int. Cl.
*G01N 35/04* (2006.01)
*G01N 35/00* (2006.01)
(Continued)

(52) U.S. Cl.
CPC .............. *G01N 35/04* (2013.01); *G01N 33/49* (2013.01); *G01N 35/00732* (2013.01);
(Continued)

(58) Field of Classification Search
CPC ..................... G01N 2035/00752; G01N 35/10
See application file for complete search history.

(56) References Cited

U.S. PATENT DOCUMENTS

| 5,171,977 | A |   | 12/1992 | Morrison |          |
|-----------|---|---|---------|----------|----------|
| 5,224,585 | A | * | 7/1993  | Blanco   | B01L 9/06 |
|           |   |   |         |          | 198/690.1 |

(Continued)

FOREIGN PATENT DOCUMENTS

| CA | 2833258 A1 * | 10/2012 | ............... G06T 7/62 |
| CA | 2833258 A1   | 10/2012 |                           |

(Continued)

OTHER PUBLICATIONS

International Search Report / Written Opinion for PCT/CA2017/050314 dated Mar. 9, 2017.

*Primary Examiner* — Matthew D Krcha
(74) *Attorney, Agent, or Firm* — Bereskin & Parr LLP/S.E.N.C.R.L., s.r.l.; Tony Orsi

(57) ABSTRACT

Various embodiments are described herein for an apparatus and method for indicating at least one property related to an object. Detection data and optionally input data are received for the at least one property related to the object and at least one light property that corresponds to the at least one property related the object based on the detection signal is determined using a processing unit. A light is then generated (Continued)

and projected to illuminate and/or surround at least a portion of the object, the light being based on the at least one light property to indicate the at least one property related to the object.

36 Claims, 10 Drawing Sheets

(51) Int. Cl.
   *G01N 35/10* (2006.01)
   *G01N 33/49* (2006.01)

(52) U.S. Cl.
   CPC ... *G01N 35/10* (2013.01); *G01N 2035/00752* (2013.01); *G01N 2035/041* (2013.01); *G01N 2035/0441* (2013.01)

(56) References Cited

U.S. PATENT DOCUMENTS

| | | | |
|---|---|---|---|
| 5,734,464 A | 3/1998 | Gibbs | |
| 6,811,531 B2 | 11/2004 | Moscone, Sr. | |
| 8,216,511 B2 | 7/2012 | Noguchi et al. | |
| 8,482,720 B2 | 7/2013 | Horsch et al. | |
| 8,663,557 B2 | 3/2014 | Tanoshima et al. | |
| 9,423,408 B2 | 8/2016 | Triva | |
| 9,505,507 B2 | 11/2016 | Yamagata et al. | |
| 2004/0265173 A1 | 12/2004 | Matsumoto et al. | |
| 2006/0000296 A1 | 1/2006 | Salter | |
| 2006/0178600 A1 | 9/2006 | Kennedy et al. | |
| 2006/0218001 A1 | 9/2006 | Mallett et al. | |
| 2006/0263258 A1 | 11/2006 | Harris et al. | |
| 2008/0097406 A1 | 4/2008 | Freed | |
| 2009/0124015 A1* | 5/2009 | Dussi | G06F 3/04817 436/43 |
| 2009/0129990 A1 | 5/2009 | Kokawa et al. | |
| 2009/0142844 A1 | 6/2009 | Le Comte | |
| 2010/0028124 A1 | 2/2010 | Lackner et al. | |
| 2012/0001729 A1 | 1/2012 | Goncalves Guedes | |
| 2013/0129166 A1 | 5/2013 | Muller et al. | |
| 2016/0025756 A1* | 1/2016 | Pollack | G01N 35/00603 436/47 |
| 2016/0349179 A1 | 12/2016 | Rochette et al. | |

FOREIGN PATENT DOCUMENTS

| | | |
|---|---|---|
| CA | 3017021 A1 | 9/2017 |
| CN | 2935158 Y | 8/2007 |
| CN | 101256149 | 9/2008 |
| CN | 202263728 U | 6/2012 |
| CN | 104330348 A | 2/2015 |
| CN | 104330362 A | 2/2015 |
| CN | 105438709 A | 3/2016 |
| CN | 205413111 U | 8/2016 |
| CN | 106093444 A | 11/2016 |
| CN | 103482189 B | 1/2017 |
| EP | 1591785 A2 | 11/2005 |
| EP | 2665346 A2 | 11/2013 |
| EP | 2889627 A1 | 7/2015 |
| JP | 4737910 B2 | 8/2011 |
| KR | 1020070073682 A | 7/2007 |
| WO | 2012097971 A1 | 7/2012 |
| WO | 2015112798 A1 | 7/2015 |
| WO | 2017152285 A1 | 9/2017 |

* cited by examiner

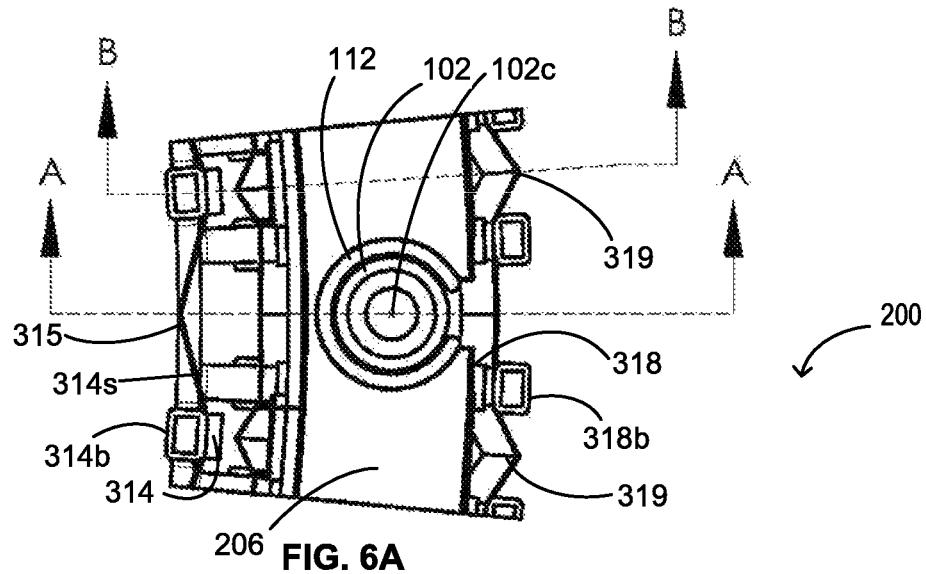
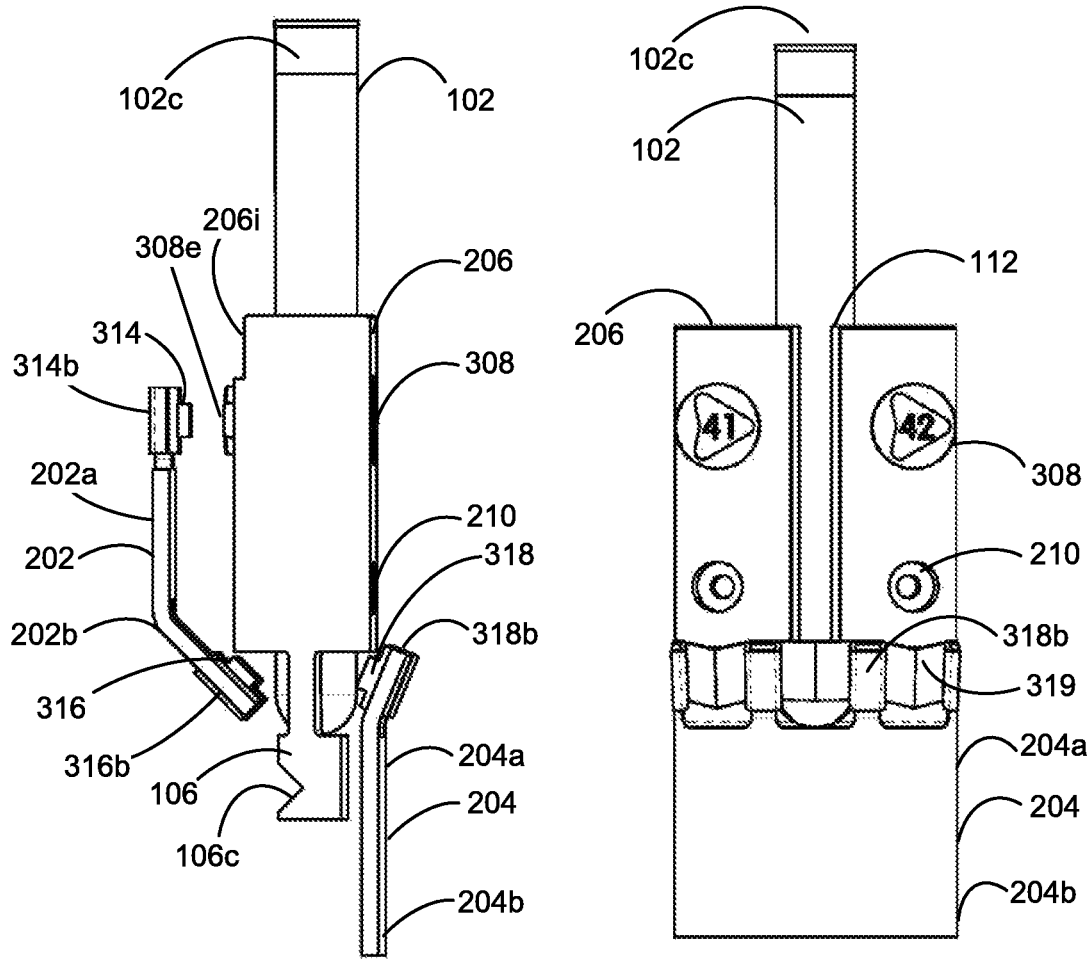
FIG. 6A
FIG. 6B
FIG. 6C

APPARATUS AND METHOD FOR INDICATING AT LEAST ONE PROPERTY RELATED TO AN OBJECT

CROSS-REFERENCE TO RELATED APPLICATION

This application claims the benefit of U.S. Provisional Patent Application No. 62/305,572 filed Mar. 9, 2016; the entire contents of Patent Application No. 62/305,572 are hereby incorporated by reference.

FIELD

Various embodiments are described herein that generally relate to apparatuses, and methods for indicating at least one property related to an object.

BACKGROUND

When dealing with a large number of samples, operations are typically performed on the samples based on one or more properties of the samples. Typically, these properties are noted manually, which is cumbersome and error prone. For example, in the medical field, it is often required to analyze samples of tissue or blood from persons or animals that are obtained and stored. Blood analyzers are used to perform this analysis as well as perform unique specialized tests and often take up large amounts of space. As a result, there are typically several blood analyzers that may be located on different floors of a building. Accordingly, when a lab technician receives a set of blood samples to be analyzed, the technician may need to know, for example, to which of the blood analyzers to send a given blood sample. For example, the technician may need to know that blood sample X must go to blood analyzer Y which is on floor Z. Therefore, for every blood sample, the technician may need to enter an identification number of the blood sample into a device, and then read and interpret resulting textual information that is provided by the device in order to determine to which blood analyzer the blood sample should be sent to or whether the blood sample must be sent to another lab for further processing. This process is time consuming and prone to human error.

SUMMARY OF VARIOUS EMBODIMENTS

In a broad aspect, at least one embodiment described herein provides a method of indicating at least one property related to an object, the method comprising: detecting the at least one property related to the object and optionally receiving input data for the at least one property related to the object using a detector and generating a detection signal including at least one of the detection data and the input data; determining at least one light property that corresponds to the at least one property related the object based on the detection signal using a processing unit; producing a light control signal based on the determined at least one light property; and generating and projecting a light based on the light control signal to illuminate and/or encompass the object with the light and indicate the at least one property related to the object.

In at least some embodiments, the object may comprise one of a container, a solid, a gas, a liquid, a sample, a sample within a container, a surface of an item and a body of an item.

In at least some embodiments, the property related to the object may comprise one or more of a status of the object, a destination of the object, a physical property of the object, a chemical property of the object, a time property of the object, a quantitative property of the object, a qualitative property of the object, a test status for the object, or a status of an apparatus that is performing the method.

In at least some embodiments, the method may comprise generating the light have a certain color to indicate the at least one property related to the object.

In at least some embodiments, the method may comprise generating the light to have a constant intensity or to have a varying intensity by pulsing the light, strobing the light, flashing the light or sequentially varying the light according to a predetermined pattern to indicate the at least one property related to the object.

In at least some embodiments, the method may comprise generating the light electrically, atomically, biologically, chemically and/or percussively.

In at least some embodiments, the method may comprise generating the light adjacent to the object or remotely from the object.

In at least some embodiments, the method may comprise generating the light to shine directly towards the object or projecting the generated light towards the object by using optical coupling.

In at least some embodiments, the method may comprise determining the at least one light property by reading a portion of the detection data or the input data obtained from performing detection on the object, by comparing a portion of the detection data or the input data to one or more thresholds, by using logic rules on a portion of the detection data or the input data, by using a portion of the detection data or input data as an index into a database or by obtaining at least one of time and date information in at least one of the detection data and the input data; or by using at least one of the time and date of at least one of when the detection was performed and the input data was obtained.

In some embodiments, the object may include a marker having object information and the method comprises detecting the marker to include the object information in the detection data, and using a portion of the object information for the at least one property related to the object or using the portion of the object information to search a database for the at least one property related to the object.

In some embodiments, the object information may comprise at least one of tests to be performed on the object, and a destination for the object as the at least one property related to the object.

In at least some embodiments, the method may comprise moving the object linearly or rotationally to the detector for detection or moving the detector linearly or rotationally to the object for detection, wherein the movement of the object or the detector is along a one dimensional axis, a two dimensional or a three dimensional axis including a vertical or horizontal axis.

In at least some embodiments, the method may comprise generating the light with a first color to indicate that the object has successfully undergone the detection act and generating the light with a second color to indicate that there has been an error in performing the detection act on the object.

In at least some embodiments, the object may be one of a biological sample, an oil sample, a gas sample, a soil sample, a solid sample, a liquid sample, a mineral sample and food and the detection comprises testing the object for a condition and generating the light to indicate that the object has passed or failed the condition.

In at least some embodiments, the method may comprise using at least one of a different light color, a different light intensity or a different lighting effect to indicate a severity of the test result.

In at least some embodiments, the method may comprise using a sample container to hold the object, and the sample container is received in a sample container holder that is moved to be adjacent to the detector for determining at least one property for the object.

In at least some of these embodiments, sample container information data and the at least one property comprises at least one of testing information for the sample in the sample container, and a destination for the sample container.

In a broad aspect, at least one embodiment described herein provides an apparatus for indicating at least one property related to an object, the apparatus comprising a detector for generating detection data and optionally receiving input data for the at least one property related to the object and generating a detection signal including at least one of the detection data and the input data; a processing unit for receiving and analyzing the detection signal for determining at least one light property that corresponds to the at least one property related to the object and producing a light control signal based on the determined at least one light property; and a lighting unit for generating and projecting a light based on the light control signal to illuminate and/or encompass at least a portion of the object with the light and to indicate the at least one property of the object.

In at least some embodiments, the lighting unit may be configured to generate the light to have a certain color to indicate the at least one property related to the object.

In at least some embodiments, the lighting unit may be configured to generate the light to have a constant intensity or to have a varying intensity by pulsing the light, strobing the light, flashing the light or sequentially varying the light according to a predetermined pattern to indicate the at least one property related to the object.

In at least some embodiments, the lighting unit may be configured to generate the light electrically, atomically, biologically, chemically and/or percussively.

In at least some embodiments, the lighting unit may comprise at least one light source for generating the light and the at least one light source is adjacent to or remotely disposed from the object and is oriented to project the generated light towards and/or around the object.

In at least some embodiments, the lighting unit may comprise at least one light source for generating the light and the at least one light source is adjacent to or remotely disposed from the object, and the apparatus includes at least one optical coupler to project the generated light towards and/or around the object.

In at least some embodiments, the processing unit may be configured to determine the at least one light property related to the object by reading a portion of the detection data or the input data in the detection signal, by comparing a portion of the detection data or the input data to one or more thresholds, by using logic rules on a portion of the detection data or the input data, by using a portion of the detection data or input data as an index into a database or by obtaining at least one of time and date information in at least one of the detection data and the input data or by using at least one of the time and date of at least one of when the detection was performed and input information was obtained.

In at least some embodiments, the object may include a marker having object information, the detector is configured to detect the marker and include the object information in the detection data, and the processing unit is configured to use a portion of the object information for the at least one property related to the object or to use the portion of the object information to search a database for the at least one property related to the object.

In at least some embodiments, the apparatus may comprise a moving portion to move the object linearly or rotationally to the detector for detection or to move the detector linearly or rotationally to the object for detection, wherein the movement of the object or the detector is along a one dimensional axis, a two dimensional or a three dimensional axis including a vertical or horizontal axis.

In at least some embodiments, the apparatus is stationary and the object is located in close proximity to the detector for detection.

In at least some embodiments, the lighting unit may be configured to generate the light with a first color to indicate that the object has successfully undergone detection and to generate the light with a second color to indicate that there has been an error in performing detection on the object.

In at least some embodiments, the lighting unit may be configured to generate the light with at least one of a different light color, a different light intensity or a different lighting effect to indicate a severity of a test result.

In at least some embodiments, the apparatus may further comprise a housing and at least one object holder coupled to the housing for holding at least one object.

In at least some embodiments, the apparatus may comprise a ring that is rotatably mounted to the housing, the ring comprising a plurality of object holders, and the lighting unit comprising a plurality of light sources mounted to the object holders, to the housing, to the ring or to a base portion of the apparatus, where each light source is addressable to a given object.

In at least some embodiments, during use the ring may be rotated to bring a given object holder having a given object adjacent to the detector for determining the at least one property for the given object.

In at least some embodiments, the light source may comprise at least one RGB LED to provide light for at least one object.

In at least some embodiments, the object may be a sample container and the object holder comprises a receptacle with an insert for receiving the sample container, the insert being transparent or translucent and generated light is optically coupled to the insert for illuminating the object.

In at least some of these embodiments, the sample container may be a test tube having a sample.

In at least some of these embodiments, the apparatus may comprise a rear light support bracket for mounting at least one of the light sources on a surface thereof facing the receptacle, and a front light support bracket for mounting at least another of the light sources on a surface thereof facing the receptacle.

In at least some of these embodiments, an additional light source may be mounted on a lower portion of the rear light support bracket facing the receptacle to illuminate a lower portion of the sample container during use.

In at least some of these embodiments, the sample container holder may comprise an insert that is disposed within the receptacle and is transparent or translucent to transmit light during use.

In a broad aspect, at least one embodiment described herein provides an apparatus for identifying a first characteristic of at least one sample container, the apparatus comprising: a base; a processing unit; a rack rotationally mounted to the base; a plurality of sample container holders disposed around a perimeter of the rack; a detector mounted to the base and in electronic communication with the processing unit; and a plurality of light sources disposed in at least one of the base and the rack, each of the light sources corresponding to one of the sample container holders.

In at least some of these embodiments, when one sample container is placed into one of the sample container holders and a scan sequence of the apparatus is initiated, the rack is configured to rotate and move the sample container to the detector; the detector is configured to detection a marker of the sample container and generate a detection signal that includes data about the sample container; the processing unit is configured to analyze the detection signal, determine a property of the sample container and generate a light control with a light property that corresponds to the property of the sample container; and the light control signal causes the light source associated with the sample container to generate a light signal having the light property and the light is projected towards and illuminates and/or surrounds at least a portion of the sample container.

In another broad aspect, at least one embodiment described herein provides a sample container holder for identifying a property of a sample container, the sample container holder comprising: a body; a receptacle for receiving the sample container; and a light source for indicating the property of the sample container; wherein the receptacle extends into the body, the light source is mounted to the body, a light emitted by the light source is projected towards and illuminates and/or surrounds at least a portion of the body, and the light source is operable by a light control signal receivable at an input of the light source.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 6A-6C show plan, side and front views, respectively, of the sample container holder of FIG. 4 that is used in the apparatus of FIG. 3.

Figure 1:
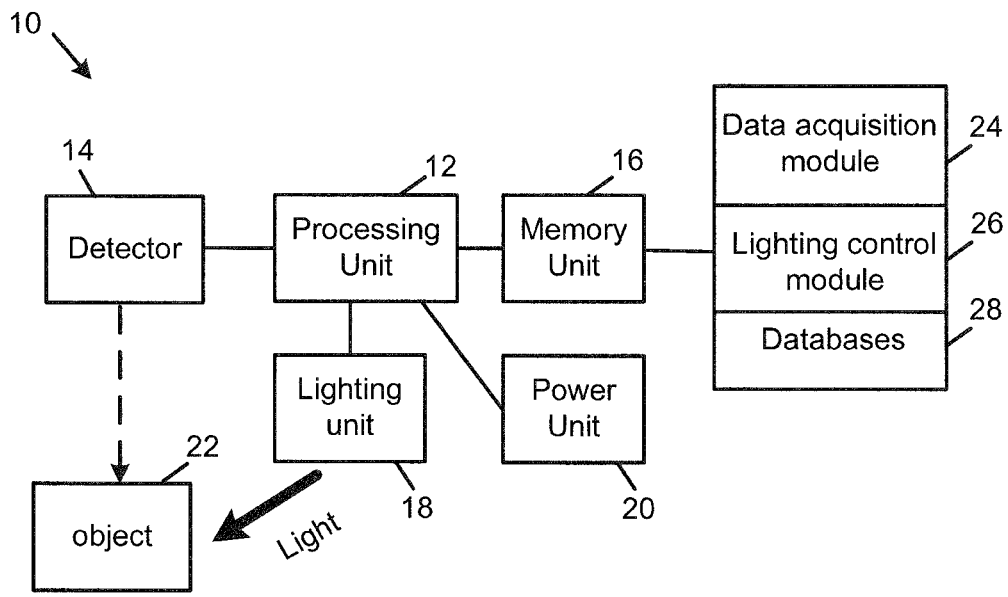
FIG. 1 is a block diagram of an example embodiment of an indication apparatus for indicating at least one property related to an object.

Further aspects and features of the embodiments described herein will appear from the following description taken together with the accompanying drawings.

DETAILED DESCRIPTION OF THE EMBODIMENTS

Various apparatuses or methods will be described below to provide an example of at least one embodiment of the claimed subject matter. No embodiment described below limits any claimed subject matter and any claimed subject matter may cover methods or apparatuses that differ from those described below. The claimed subject matter is not limited to apparatuses or methods having all of the features of any one apparatus or process described below or to features common to multiple or all of the apparatuses or methods described below. It is possible that an apparatus or method described below is not an embodiment of any claimed subject matter. Any subject matter that is disclosed in an apparatus or process described below that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or optical connotation. For example, as used herein, the terms coupled or coupling can indicate that two elements or devices can be directly connected to one another or connected to one another through one or more intermediate elements or devices via an electrical element, electrical signal (either wired or wireless), optical signal or a mechanical element, such as, tubing, pipes, brackets and the like depending on the particular context.

It should also be noted that, as used herein, the wording "and/or" is intended to represent an inclusive-or. That is, "X and/or Y" is intended to mean X or Y or both X and Y, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may be construed as including a certain deviation of the modified term if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

The example embodiments of the apparatus or methods described in accordance with the teachings herein may be implemented as a combination of hardware and software. For example, the embodiments described herein may be implemented, at least in part, by using one or more computer programs, executing on one or more programmable devices comprising at least one processing element, at least one memory element and at least one storage element (i.e. at least one volatile memory element and at least one non-volatile memory element). The apparatus may have input devices including at least one of a touch screen, a keyboard, a mouse, buttons, keys, sliders and the like, as well as one or more of a display, a speaker, a printer, and the like depending on the implementation of the apparatus.

It should also be noted that there may be some elements that are used to implement at least part of the embodiments described herein that may be implemented via software that is written in a high-level procedural language such as object oriented programming. The program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a computer readable medium such as, but not limited to, ROM, magnetic disk, optical disc, or a computing device that is readable by a general or special purpose programmable device having a processor, an operating system and the associated hardware and software that is necessary to implement the functionality of at least one of the embodiments described herein. The software program code, when read by the computing device, configures the computing device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Described herein are various example embodiments for apparatuses and methods that may be used to determine or detect at least one characteristic for a sample container and then shine a corresponding light to provide a visual indicator of the at least one characteristic. In some embodiments, the light may be shone to illuminate the sample container.

Referring now to FIG. 1, shown therein is a block diagram of an example embodiment of an indication apparatus 10 for determining and indicating at least one property related to an object 22. The object 22 may be a container, a sample, a container including a sample, a surface of an item, or a body of an item. The apparatus 10 is provided as an example and there may be other embodiments of the apparatus 10 with different components or a different configuration of the components than those described herein but is still covered by the scope of the appended claims. The apparatus 10 further includes at least one power supply connected to various components of the apparatus 10 for providing power thereto as is commonly known to those skilled in the art.

The property that is to be indicated can be one or more of a status of the object 22, a destination of the object 22, a physical property of the object 22, a quantitative property of the object 22, a qualitative property of the object 22, a chemical property of the object 22, a time property of the object 22, a test status for the object 22, or a status of the apparatus 10.

The object 22 can be a container, a solid, a gas, a liquid, a sample, a sample within a container, a surface of an item, or a body of an item depending on the particular use case scenario for the apparatus 10.

The apparatus 10 comprises a processing unit 12, a detector 14, a memory unit 16, a lighting unit 18 and a power unit 20. In alternative embodiments, the apparatus 10 may further comprise a user interface, a display, a network connection and a wireless radio unit (all not shown). The memory unit 16 comprises software code for implementing an operating system and various programs for the operation of the apparatus 10 including a data acquisition module 24, a lighting control module 26 and one or more databases 28. Modules 24 and 26 will be described in greater detail with respect to FIGS. 1 and 2. Some of the modules may be combined or further sub-divided in alternative embodiments.

In general, the detector 14 detects at least property related to the object 22 and generates a detection signal. In some embodiments, the detector 14 may optionally receive input data for the at least one property related to the object or an input unit including a touch display, buttons, or wired or wireless input may be used to obtain the input data. Accordingly, the detection signal includes at least one of the detection data and optionally the input data. The processing unit 12 receives and analyzes the detection signal for determining at least one light property that corresponds to the at least property. After this determination is made, the processing unit 12 produces a corresponding light control signal The lighting unit 18 receives the light control signal and generates a light having the at least one light property specified by the light control signal to indicate the at least one property related to the object 22. In some embodiments, the lighting unit 18 may shine this light directly on the object 22 to illuminate and/or encompass (e.g. surround or envelope) at least a portion of the object 22. In other embodiments, the light may be optically coupled and projected onto the object 22. It has been found that illuminating or encompassing at least a portion of the object 22 reduces error in object handling when there are multiple objects for which a property is indicated by a light property and the objects need to be handled based on the corresponding light property.

The processing unit 12 controls the operation of the apparatus 10 and can be any suitable processor, controller or digital signal processor that can provide sufficient processing power depending on the configuration and operational requirements of the apparatus 10 as is known by those skilled in the art. For example, the processing unit 12 may be a high performance general processor. In alternative embodiments, the processing unit 12 may include more than one processor with each processor being configured to perform different dedicated tasks. In alternative embodiments, specialized hardware can be used to provide some of the functions provided by the processing unit 12, such as at least one ASIC and/or FPGA.

The detector 14 may be any device that is able to obtain information for the at least one property related to the object 22. For example, the object 22 may be a container that has an identification marker that provides information about at least one property of the container or a sample within the container and the detector 14 may be a scanner or a computer vision unit that is able to scan and detect the identification marker and generate the detection signal with information (i.e. data) about the identification marker. For example, the identification marker may be a label that has various pieces of information such as, but not limited to, a number, a name, a status or a destination for the object 22. At least one of these pieces of information data may be a property of the object 22 that can be indicated using at least one light property.

The detector 14 and the processing unit 12 may be configured to determine light properties depending on information that is given about the object and scanned by the detector 14 optionally including input data, or based on time/date information of when the object was created and/or processed by the apparatus 10, or based on further processing detection data, operational data and/or sensor data where the detection data is generated by the detector 14 upon scanning the object 22 or detecting a certain property or conditions of the object 22, the operational data is obtained by checking the apparatus for certain conditions, and sensor data may be obtained using sensors (if sensors are used with the apparatus). The conditions may be determined or may be varied depending on the application (i.e. use case scenario) of the apparatus 10 and the conditions may be variable or may be fixed.

In other example embodiments, the detector 14 may be a scale which detects a weight of the object 22. In this case, the weight is the property of the object 22 that is then indicated by using at least one light property.

In another example embodiment, the object may be a liquid and the detector 14 may be detecting the volume of the liquid. For example, the detector 14 may be an ultrasonic device that can measure liquid level. The determined liquid level may then be indicated using at least one light property.

In another example embodiment, the detector 14 may be detecting the time associated with the object 22 to determine if the object or contents contained therein have expired. In this example, the identification marker is a timestamp, such as a date and/or time in the form of numbers and/or letters and the detector 14 comprises a scanner and/or camera that reads the timestamp and the detected timestamp may then be compared to a reference timestamp to determine if the object 22 or contents therein are old (e.g. if the current date is later than the detected timestamp) and at least one light property is generated and displayed to indicate this property.

In another example embodiment, the detector 14 may be implemented to perform a test on the object 22 or a sample therein and the results of the test can be indicated by using at least one light property. For example, the object 22 may be a biological sample such as a blood sample, a urine sample, or a hair sample, and the detector 14 may test the object for a particular condition and provide a pass or fail result if the object has or doesn't have the condition. The object 22 may be contained in a test tube, a vial, a blood bag, or on a glass slide, for example.

Alternatively, the object may be a chemical sample, a soil sample or a mineral sample that the detector 14 tests for a particular condition, contaminant or toxin and provides a pass or fail result if the object has or doesn't have the contaminant or toxin, respectively, for example. In one example embodiment, the object 22 may be contained in, but is not limited to, a test tube, a vial, a beaker, a container, or an oil tanker.

Alternatively, the object 22 may be a food sample that the detector 14 tests to see if it has spoiled or has a particular contaminant and provides a pass or fail result if the object 22 has or has not spoiled or has or doesn't have the contaminant, respectively, for example. In one example embodiment, the object 22 may be contained in a food container, such as a milk bottle or a juice carton. Alternatively, the object 22 can be over the counter and prescription drugs that may be checked for expiration and then illuminated with a particular light color to indicate whether or not expiration has occurred.

Alternatively, the object 22 may be a product that is part of an inventory and the property that may be identified may be product quality, product expiration or some other property of the product. The product can be a variety of items such as, but not limited to, one or more of food, drink, chemical, paint, and battery items.

Alternatively, the object 22 may be an item that is not enclosed within a container but is free-standing. For example, the object 22 can be an item such as a hair sample that may be used in DNA testing and classification. A test or classification may be performed on the item and the result can be indicated by using at least one light property.

Alternatively, the object may be a layer of material on the surface of an item such as paint or an ink sample on a substrate. The object can be tested or classified for one or more of, for example, colour corrected status, coverage and density, and the test or classification result can be indicated by using at least one light property.

Alternatively, the object may be a sample that is taken from a container and placed on a slide upon which it is processed. In this case, the object can also be considered to be a layer of material that can be tested for a particular condition or lack thereof and the test results can be indicated by using at least one light property.

Alternatively, the object 22 may be an RF coil that may be etched on a substrate and the object may be tested for proper operation, which may include testing if the RF coil resonates within a given frequency. The RF coil may be used in RFID tags, EMID tags other electronic devices. The test result can be indicated by using at least one light property.

In other embodiments, the object 22 may be a beverage container and the property may be temperature status that may be confirmed visually using at least one light property rather than using hand written chinagraph markings on the container. In this case, a time counter may be used to count the time since the beverage was prepared and different ranges of times can be shown visually using different light properties, such as different light colors. The detector 14 may detect which range the count being kept by the time counter is in for which a particular color is assigned. For example, when the count is less than about 15 minutes, a white light may be displayed, when the count is between about 15-30 minutes a green light may be displayed, when the count is between about 30-60 minutes a yellow light may be shown which may indicate that the beverage needs to be replaced soon, and when the count is over 60 minutes a red light may be displayed, which may indicate that immediate replacement is needed. Alternatively, the detector may be a temperature sensor that measures the temperature of the beverage and a light property is used to indicate the range that the temperature is in, similar to the count range example just given.

The memory unit 16 includes volatile and non-volatile computer storage elements such as, but not limited to, one or more of RAM, ROM, one or more hard drives, one or more flash drives or some other suitable data storage elements. The memory unit 16 may be used to store an operating system and programs as is commonly known by those skilled in the art. For instance, the operating system provides various basic operational processes for the apparatus 10 and the programs include various operational and user programs so that a user can interact with the apparatus 10 to process the object 22.

The lighting unit 18 may comprise any suitable light generating element that may generate and project a light to illuminate and/or encompass at least a portion of the object 22 with the light wherein the light has at least one light property, such as a particular light color that may be selected from several different light colors, a light intensity selected from several different light intensities as well as lighting effects that comprise at least one of pulsing, strobing, or flashing the same color, or at least one of pulsing, strobing or flashing alternating different colors. The light property (e.g. light color, light intensity and/or lighting effect) can be determined based on a number of different factors, conditions or inputs that can be provided to or determined by the processing unit 12.

The lighting unit 18 may comprise at least one light source, and possibly switching elements, to provide at least one of the light colors, one of the light intensities and one of the lighting effects. Accordingly, the lighting unit 18 may be configured to generate a light that is constant, that varies in intensity, a pulsed light, a strobe light, or a flashing light that flashes according to a particular sequence.

The light source(s) used in the lighting unit 18 may be a multi-color light emitting diode (LED) that can emit various light colors, or an array of LEDs where each LED can emit light having a unique color, or an assembly of Red, Green and Blue LEDs that are controlled together to emit a particular light color. In other embodiments, the light source may comprise a collection of different colored incandescent light bulbs, a collection of different colored fluorescent light bulbs, or a neon light. Accordingly, depending on how the light source is implemented, the displayed light may be generated electrically, atomically, biologically, chemically or percussively.

The lighting unit 18 may be disposed on the apparatus 10 such that if the apparatus 10 is hand-held and is pointed towards the object 22, then when the detector 14 scans the object 22 to detect a particular property of the object 22 and the processing unit 12 determines the corresponding light property, then the lighting unit 18 may receive a light control signal from the processing unit 12 to shine or project a light having the corresponding light property directly towards at least a portion of the object 22 or the light can be optically coupled so that the light is shone or projected towards at least a portion of the object 22.

For example, the object 22 may be a surface or item that is being scanned for a concentration of one or more bio markers. In these cases, the detector 14 contains appropriate hardware to be able to detect the concentration of the one or more bio markers and the light can be generated and projected onto the surface or item with a light property indicating the concentration of the one or more bio markers. For example, a surface or item that is clean can be illuminated with a green color, whereas if the surface or item has bacteria concentration above a certain threshold it can be illuminated with a red color.

In an alternative embodiment, the apparatus 10 may have an object holder within which or upon which the object 22 may be placed during processing. In this case, the lighting unit 18 may be disposed on the apparatus 10 such that it is oriented towards the object holder to illuminate at least a portion of the object 22 after it is processed by the detector 14. For example, in some embodiments, the lighting unit 18 may comprise a light source that is oriented so that it shines light towards one of the sides of the object 22 or the lighting unit 18 may be disposed below the object holder so that when the object 22 is placed in or on the object holder and processed, the light source shines a light having the at least one determined light property upwards through the object holder. In other embodiments, other orientations for the lighting unit 18 may be possible such that the light source does not necessarily illuminate the object 22 but rather shines a light that can be seen by an operator of the apparatus 10 and is preferably in close proximity to the object 22 that is being processed. Accordingly, the light source can be disposed such that the light is generated remotely or directly in relation to the position of the object 22.

The processing unit 12 is electrically coupled with the lighting unit 18 to provide the light control signal to the lighting unit 18 to control at least one light property such as the light color and/or any lighting effects of the light that is generated by the lighting unit 18 during use. The format for the light control signal depends on the implementation of the lighting unit 18. For example, if the lighting unit 18 is implemented with an LED array, then the light control signal may be provided by the processing unit 12 to a switching unit to activate one of the LEDs in the LED array. As another example, if the lighting unit 18 is implemented using a red LED, green LED and blue LED combination, then the light control signal may be three separate signals that control the intensity of the emitted light from the red, green and blue LEDs to control the light color of the emitted light signal.

In some embodiments, there may be several light sources in the lighting unit 18 that each has a multi-color LED. In these embodiments, the lighting unit 18 may further include and a light controller (not shown) that communicates with the processing unit 12 for controlling the light emitted by the lighting unit 18.

The power unit 20 can be any suitable power source that provides power to the apparatus 10 such as a power adaptor or a rechargeable battery pack depending on the implementation of the apparatus 10 as is known by those skilled in the art. In other embodiments, the power unit 20 can be a DC regulated power supply.

As previously mentioned, the object 22 may be contained within or on a suitable container and the shape of the container depends on the object as well as the particular application. For example, in the medical field, the object may be a biological sample such as a blood sample, a urine sample or a hair sample, and the container may be a test tube, a slide, a vial, a bag or other suitable container. In other potential applications, the container may take other forms, such as a bottle for oil, gas and/or soil applications, or a food package or drink package (such as a bottle, can, or drink box) and the like in the food industry. In other examples, there may not be a container and the object 22 may be placed on a surface for processing. For example, this may occur if the object 22 is a brick, a physical solid piece of another object, or a lump of material such as a lump of mineral.

As mentioned previously, the apparatus 10 may include an object holder (not shown) which holds the object 22 while it is processed by the apparatus 10. The object holder may be a channel or a receptacle that is sized to receive the object 22 or a container that may hold the object 22. In some cases, the object holder may also include a retaining element to hold the object 22 in place once it has been inserted into or onto the object holder. For example, a cantilever spring may be used. In other embodiments, the object holder may be a gripping element such as a clamp that may receive the object 22. In some embodiments, the gripping element may have actuators so that the gripping element may orient the object 22 so that a label or other visual indicator on the object 22 is oriented to be facing an input of the detector 14, such as a sensor or a camera.

The object holder may be adjacent to the detector 14 so that the object 22 can be processed by the detector 14 after the object 22 is engaged by the object holder. In this case, the lighting unit 18 may also be disposed adjacent to the detector 14 so that it is facing toward the object 22 when it is placed within the object holder.

In other embodiments, the object holder may be able to hold several objects 22 at the same time, in which case the object holders described previously may be replicated in a linear array or a circular array (i.e. a ring format). In this case, if there is one light source that is disposed near the detector 14, then the object holder may rotate or slide linearly to bring a particular object 22 to the detector 14 for processing after which point the lighting unit 18 near the detector 14 generates a light having the light property that corresponds to the property of the object to be identified.

In other embodiments in which the object holder can hold several objects 22 at the same time, the lighting unit 18 may have an array of light sources so that there is one light source for each object 22 that lights up when that particular object 22 is processed. The processing unit 12 (optionally in conjunction with a light source controller) controls each light source independently. In some of these embodiments, the object holder may also be rotated, linearly translated or otherwise moved to bring a particular object 22 to the detector 14 in order to be processed.

For example, the object holder may be placed on a rotating ring that is rotated by an actuator, such as a rotating disc, that is powered by a motor and the detector 14 is adjacent to an inner or outer portion of the ring and faces towards the object holder as it is rotated by the detector 14. Alternatively, there may be a circular track, the detector 14 may be adjacent to either an outer portion or an inner portion of the track and face towards the track, and a bottom portion of the ring may have object holders that engage the track with one or more vertical gear wheels that are turned by a motor thereby rotating the object holders.

Alternatively, in some of these rotating embodiments, the object holders may be stationary and the detector 14 may be rotated to process each object 22 as it passes by the object. For example, the detector 14 may engage the circular track with a gear wheel and be rotated along an inner or an outer edge of the track where the sample container holders are maintained in a stationary position.

In any of these embodiments in which the object or the detector may move, the movement of the object or the detector may be along a one dimensional axis, a two dimensional or a three dimensional axis including a vertical or a horizontal axis.

In at least some embodiments, the generated light may have a particular color that indicates a property related to the object. For instance, a first light color, such as blue, may be used to indicate that the object holder is empty and is ready to receive a new object 22. In some embodiments, a second light color may be used to indicate that the object holder has been loaded with a new object 22 and must still be processed. Alternatively, no light may be shone or projected in this case.

In at least some embodiments, where the object is a container or is within a container and the container has a lid, such as a cap, when the object 22 is a test tube, then the lighting unit 18 may shine or project a light onto or around at least a portion of the object 22 with a particular color to identify that the object 22 has a cap, it has been processed by the apparatus 10 and is ready for further handling. Various sensors may be used to detect if the object 22 has a cap as will be described in further detail with regards to the apparatus of FIG. 3. Accordingly, it is understood that in at least one embodiment, the apparatus 10 may have at least one sensor (see FIG. 8 for an example of container height and cap sensors) for sensing a certain condition. Alternatively, the lighting unit 18 may shine or project a light onto and/or around at least a portion of the object 22 having another light color to indicate an error condition, which in this case may be that the object 22 has a missing cap or a cap cannot be placed on the object 22 and an operator may be visually guided to inspect the container. For example, the lighting unit 18 may shine or project a red light onto the object 22 in these error cases.

In at least some embodiments, if the object 22 is supposed to have a barcode or a label but it is missing or unreadable by the detector 14, then the lighting unit 18 may also shine or project a light color to at least a portion of the object 22 to indicate an error condition such that the object 22 cannot be processed correctly. In this case, the detector 14 may be looking for information in a specific region of the object 22 where the label or barcode is typically located but the detector 14 doesn't find any useful information at that location.

In at least some embodiments, if the object is a sample within a container that has been centrifuged, then the detector 14 may detect an identifier for the object so that the processing unit 12 can check a database to determine that the sample has been centrifuged. This property of having been centrifuged can be indicated by a light having the corresponding light color and/or other determined light property that is shone on, near or projected towards the object 22. Likewise, the database can be checked to see if the sample hasn't been centrifuged but needs to be centrifuged; this property can then be indicated with a corresponding light property. In some embodiments a sensor may be used to determine if the sample has or has not been centrifuged by sensing the homogeneity of the sample or if the sample has separate liquid phases.

In at least some embodiments, if a given object 22 has been scanned and archived into one of the databases 28, and it is ready for further handling, then the lighting unit 18 can shine a light with a particular light color and/or other determined light property to indicate this, such as the light color green. This then signifies to an operator that the object 22 may be removed from the apparatus 10 and placed in another element for further handling such as a rack.

In at least some embodiments, the object 22 may be processed by the apparatus 10 to determine its destination for further handling or testing. For example, in the case that the object 22 is a sample container that contains a biological sample that must undergo laboratory processing in which particular tests are to be conducted on the sample container at a certain destination (e.g. at a certain laboratory or medical device on a certain floor of a medical institution), then the property of the object 22 that is determined by the detector 14 in combination with the processing unit 12 and indicated by the light generated by the lighting unit 18 may be the destination of the object 22 where it will receive this further laboratory processing. In this case, the detector 14 may detect an identifier for the sample container, such as the name of the person from which the sample was taken or a barcode or other visual indicator that provides this identification information. This identification information data may then be sent to the processing unit 12 which then checks one of the databases 28 to determine particular information that is associated with the sample container, which in this example is the destination where tests are to be performed on the sample within the sample container. Within the same database 28, or within another database or lookup table, the processing unit 12 may determine which light property is associated with that particular destination and then communicates this information to the lighting unit 18 which then shines or projects a light onto at least a portion of the object 22 having the determined light property, which may be a light color. An operator may then place the sample container in the proper rack that will be sent to the determined destination for further testing.

It should be noted that the operation that was just described may be applied to the other possible use case scenarios described herein, such as for sample testing in the oil, gas, mineral or food industries. The property related to the object that is detected may be different in these different use case scenarios, but the actions performed by the detector 14, the processing unit 12 and the lighting unit 18, in conjunction with checking one of the databases 28 or lookup table, may be similar.

Therefore, in accordance with the teachings herein, at least one example embodiment is provided in which various light properties of a generated light signal may be changed to indicate at least one property related to the object 22. These light properties that may be changed include, but are not limited to, at least one of the color, light intensity or lighting effect of the light that is shone on, around, underneath, adjacent to or otherwise optically coupled with the object 22.

Furthermore, in accordance with the teachings herein, at least one example embodiment is provided in which the light property may be changed to indicate at least one property related to the object 22, which may include the processing performed by the apparatus 10. Examples of the light property include, but are not limited to, at least one of a result (or lack of a result) of a variety of conditions such as analytic testing (e.g. weight, level, color, consistency, or more complicated analysis of the object 22), or properties such as the date and/or time that the object 22 was processed or made, if the object 22 is ready for further processing or handling, if the object 22 has a new status or the destination of the object 22. With regards to the status of the object 22, this may relate to a property of the object 22 that can change with time or indicate a quality of the object 22 that may change with time. For example, the status of the object 22 may be that it is useable or expired, or that it is contaminated or not contaminated.

For example, when the objects are sample containers that contain biological samples, such as blood samples, and are processed in a hospital or laboratory setting, the conditions that can trigger a particular light property being indicated in a light signal generated by the lighting unit 18 may include, but are not limited to, at least one of if the object holder of the apparatus 10 is empty or full (in both cases where the object holder can hold one or many objects 22), whether a barcode or other identifier on the one or more objects 22 have been successfully scanned and archived (i.e. crossreferenced with one of the databases 28), and whether the objects 22 have caps placed thereon. The processing unit 12 can determine or observe the results of these queries from various inputs that it receives from the detector 14 and optionally one or more sensors (not shown) of the apparatus 10 depending on the conditions being detected. The processing unit 12 may then check with one of the databases 28 and/or preset thresholds that correspond to the detected condition and specified parameters in the lighting control module 26 to determine at least one of the color, intensity and lighting effect control parameters that are then encoded as the at least one light property in the light control signal that is sent to the lighting unit 18. At this point, the object 22 may change from being considered to be an active sample to being an archived sample that is or will soon be placed in a refrigeration unit, when the object 22 is a sample that requires refrigeration after processing.

As another example, in the use case scenario of water testing, the detector 14 may perform a vision or weight inspection of the object which is a container having a water sample to determine if the water sample is enough for the testing required (for example, the testing may be for bacteria count). For example, the detected water level may be sent to the processing unit 12 which then checks with one of the databases 28 or a lookup table for a threshold water level for comparison with the detected water level. If the detected water sample level is greater than the water level threshold, then the processing unit 12 may instruct the detector 14 to carry on with testing. If the detected water sample level is lower than the threshold level, then the processing unit 12 may configure the light control signal so that the lighting unit 18 generates and projects a flashing light having a certain color onto and/or around at least a portion of the object 22 as an alert to the operator that the water sample needs more water in order to be tested. When there is enough water in the water sample, the detector 14 may proceed with the water testing and the test results may be indicated by using certain light properties to make it easy for the operator to understand the test results. For example, the test may comprise performing a bacterial count for certain bacteria in the water sample, and the test results for bacterial content may be indicated by the lighting unit 18 by projecting light with different colors for different ranges of bacteria content. These different ranges may be stored in one of the databases 28 or a look up table that the processing unit 12 may use for comparison to the detected bacteria count to determine a corresponding color (for the light property in this case). For example, if the bacteria count is between 0-5 and is considered safe, then the lighting unit 18 may be controlled to shine or project a light with a green color, if the bacteria count is in the danger zone of 6-8 then the lighting unit 18 may be controlled to shine or project a light with a yellow color, or if the bacteria count is 9 or above and considered dangerous, then the lighting unit 18 may be controlled to shine or project a flashing light having a red color. The operator may then take different actions depending on the light color and the nature of the water test. For example, if the water sample was taken from a beach and the test results are indicated using a red light color, then the operator may call the appropriate authorities to erect the appropriate signage to warn swimmers at the beach and possibly not allow swimming at the beach if the test results are particular severe. Other ranges and/or other light colors may be used in other embodiments.

The data acquisition module 24 may be used to obtain detection data for the object 22 and optionally status data for the apparatus 10 during operation. The data acquisition module 24 may obtain the detection data and the status data from the detector 14 and optionally one or more sensors (if included in the apparatus 10). The detection data and the status data may correspond to the one or more properties and/or conditions that the detector 14, and optionally one or more sensors, is trying to determine for an object 22 and/or the operational status of the apparatus 10 itself. Accordingly, at least one analog to digital converter (ADC) (not shown) is included with the apparatus 10 to convert the detected or sensed data into digital data for further processing and/or handling. There may be an ADC that receives inputs from the detector 14 and the one or more sensors (if included) or there may be dedicated ADCs that are provided with the detector and the one or more sensors (if included) depending on the implementation of these elements.

The light output module 36 receives the detection data and the optional status data and processes both of this data to determine the one or more light properties that may be used to indicate a property of the object 22 or the operational status of the apparatus 10. The light property may include color, light intensity, and whether there are any lighting effects, which depends on how the lighting unit 18 is implemented. Once the light property is determined the light property is encoded and sent in a light control signal to the lighting unit 18 to shine or project a light corresponding to the determined light property. The processing unit 12 may determine the light property by performing at least one of: using information that is directly encoded in at least one of the detection data and the status data, comparing at least one of the detection data and the status data to a corresponding threshold for the particular property to be indicated or by using at least one of the detection data and the status data as an index into a database which provides the associated lighting property or the status data and/or the detection data may be compared to one or more thresholds or threshold ranges. It should be noted that there may be one or more light properties that are determined in some embodiments.

It should be noted that the data acquisition module 24 and the lighting control module 26 may be combined or further divided into other modules in other embodiments. Furthermore, in other embodiments, at least one of the data acquisition module 24 and the lighting control module 26 may be implemented differently than what is described herein but perform the same overall functions described herein. The data acquisition module 24 and the lighting control module 26 are typically implemented using software, but there may be some instances in which at least some of these modules may be implemented using FPGA or application specific circuitry.

The databases 28 can be used to store data for the apparatus 10 such as system settings, parameter values, and calibration data. The databases 28 may also be used to store information required for the operation of user and/or operational programs as well as the operating system such as dynamically linked libraries and the like. The databases 28 may also be used to store object data for the processed objects 22 such as a unique identifier for each object 22 and the one or more determined properties that are associated with each object 22.

Figure 2:
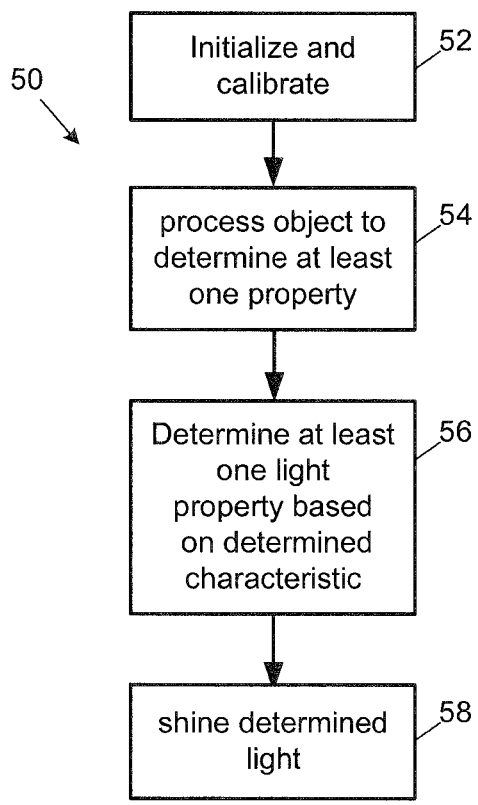
FIG. 2 is a flowchart of an example embodiment of an object indication method for indicating at least one property related to an object.

Referring now to FIG. 2, shown therein is a flowchart of an example embodiment of a sample characterization indication method 50 for determining and indicating at least one property of the object 22, a sample contained within the object 22 or the apparatus 10 that is used to process the objects 22. It should be understood that acts 54 to 60 may be performed for each object 22 that is to be processed. In other embodiments some of the acts of method 50 may be broken down into two or more acts depending on the particular use case scenario.

At act 52, the apparatus 10 is initialized for operation. This may also include calibration of the detector 14 and any sensors that may be used by the apparatus 10. The calibration may be done each time the apparatus 10 is powered up or it may be done on a periodic basis depending on whether the detector 14 and/or any sensors have parameter values that may drift over time and affect the detection data provided by the detector 14 and any sensor data provided by the sensors (if used). The calibration may include making sure that certain sensors and/or the detector 14 is properly aligned for processing the object, or monitoring the status of the apparatus 10 during use.

At act 54, an object 22 is processed by the detector 14 and optionally any sensors (if used by the apparatus 10) to determine at least one property related to the object 22. Alternatively, the determined property may be for an operational status of the apparatus 10. The property may be determined in a number of different ways as previously described depending on the particular use case scenario for the apparatus 10 and the type of object that is being processed.

At act 56, the light property that corresponds to the determined property related to the object is determined. This may be done in a variety of ways as explained previously for the operation of the apparatus 10, such as by comparing the determined object property to an associated threshold or by using the determined object property as an index into a database that specifies the associated light property. In addition, in at least some embodiments, various light colors may be used as the determined light property to indicate different conditions. For example, a certain light color may be used to indicate that there is no object 22 being processed or there an object container 22 that is empty. As another example, a different light color may be used to indicate that there is an error in processing the object 22. Alternatively, a lighting effect, as described previously for the apparatus 10, may also be used in addition to the light color to indicate a particular property, operational status of the apparatus 10 or other condition. A light control signal is generated that encodes the at least one determined light property.

At act 58, the lighting control signal is sent to the lighting unit 18 to control the lighting unit 18 to generate and project a light towards and/or around at least a portion of the object 22 to at least partially illuminate the object 22 where the light has the one or more determined light properties. As explained for the various embodiments of the apparatus 10, the light may be shone adjacent to the object 22 that is being processed or it may be shone on any portion of the object 22 being processed or it may be otherwise optically coupled to the object 22. In some embodiments, the lighting unit 18 may comprise a single light source that generates light which is projected towards each object 22 that is processed. In other embodiments, in which there are several object holders, the lighting unit 18 may comprise several light sources in which each light source is disposed near a unique object holder and generates a light that is projected onto and/or around at least a portion of the object 22 where the light has the at least one determined light property. The light for a given object 22 may be shone or projected until an operator removes the object 22 from the apparatus 10.

Figure 3:
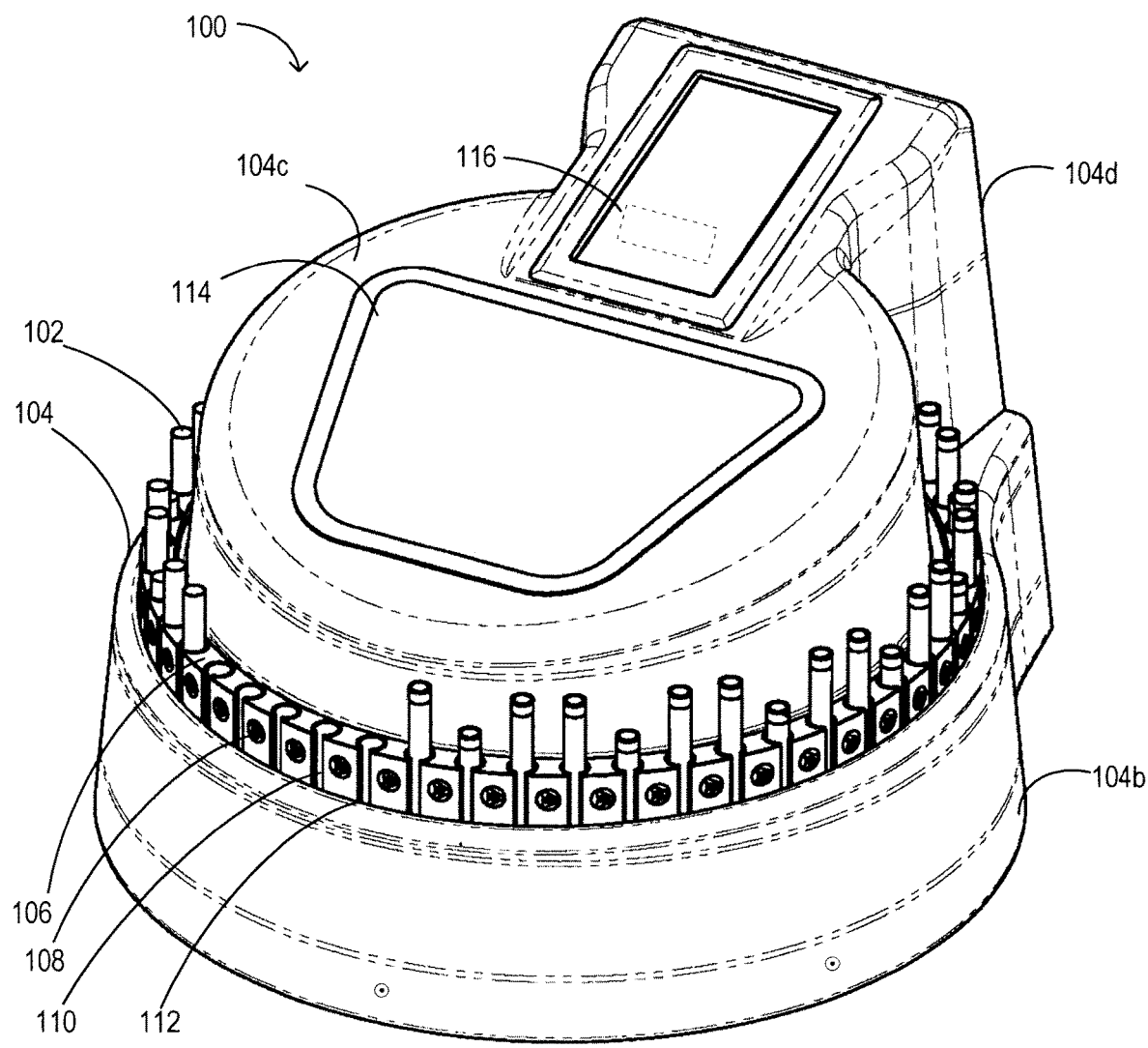
FIG. 3 is an isometric view of another example embodiment of an object indication apparatus for indicating a property of an object which is a sample container.

Referring now to FIG. 3, shown therein is an isometric view of an example embodiment of an object indication apparatus 100 for identifying at least one property related to an object. The apparatus 100 may be used in various scenarios some of which were discussed in relation to apparatus 10. For example, if the objects are sample containers and the object holders are sample container holders, then the apparatus 100 may be used for pre-analysis sorting of the sample containers in which each sample container is processed so that different lights for each sample container may be used to indicate at least one property related to a given sample container, such as at least one of the status and destination of the given sample container. The lights can have one or more light properties that are associated with a particular value of the property to visually indicate the property such as at least one of a particular light color, a particular light intensity and a particular lighting effect (e.g. pulsing, strobing, flashing, or alternating between different colors).

The apparatus 100 will be described with respect to being configured for use in a medical laboratory setting. However, it should be understood that one or more aspects of the apparatus 100 may be modified for use in other industries such as, but not limited to, the oil, gas, soil and food industries. The apparatus 100 may also be modified for use with other types of objects by modifying the object holder. For example, when the objects are sample containers, the apparatus 100, the sample containers and the sample container holders may have different sizes to accommodate different types of samples, such as oil, gas, soil or food samples, respectively. Furthermore, a detector and/or at least one sensor that may be used by the apparatus 100 may be modified to detect different properties related to the sample containers or the operational status of the apparatus 100 itself in the different use case scenarios. In addition, the databases and any preset thresholds may be altered to correspond with the particular sample containers and/or samples that are being processed in the different use case scenarios. Other modifications may be made to the apparatus 100 as was described for the apparatus 10.

Figure 8:
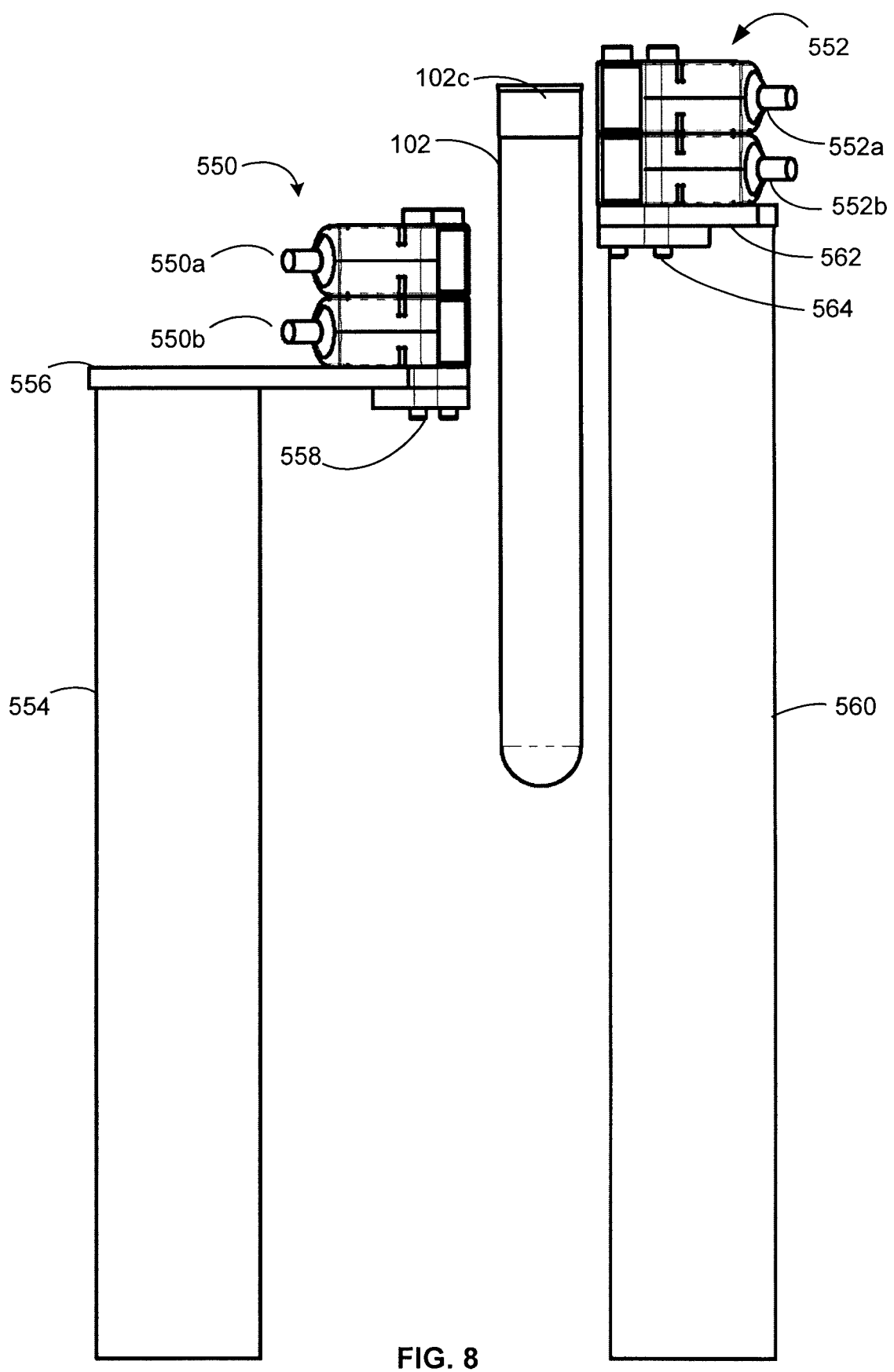
FIG. 8 is a view of sensors that may be used with the apparatus of FIG. 1 or FIG. 3 to detect capped or uncapped containers having various heights.

In the example medical use case scenario, the apparatus 100 may be used for pre-analysis sorting of sample containers 102 such as medical test tubes. The apparatus 100 comprises a housing 104 with a base 104b, a cover 104c and a detector housing 104d to house a detector (not shown). Accordingly, the detector may be mounted to an interior or exterior portion of the housing 102 similar to how sensors 550a, 550b, 552a and 552b are mounted (an example of which is shown in FIG. 8). The materials selected to make these elements may be durable, cost-effective and suited for the environment in which the apparatus 100 is operated. For example, in a medical environment, materials are selected that meet medical device regulations.

The apparatus 100 further comprises a rotatable ring 106 comprising a plurality of sample container holders 110 which may each be identified by an ID indicator 108. The ring 106 may be rotationally mounted to the base 104b and may be rotated by using a motor with appropriate mechanical coupling such as a rotating disc that engages a portion of the ring 106 such that as the disc rotates during use, the ring 106 is also rotated. The ring 106 may have a generally circular shape and the sample container holders 110 may be disposed around a perimeter of the ring 106. The ID indicator 108 may be made of transparent or semi-transparent material such that light generated by the light source that corresponds to the sample container holder can shine or be projected through at least a portion of the sample container holder (and the sample container if disposed therein) during use.

Each sample container holder 110 may also include an insert 112 (e.g. a sleeve) that is used to provide a secure fit with the sample container 102. In some embodiments, the insert 112 may also be made of transparent or semi-transparent (i.e. translucent) material so that light generated by the corresponding light source may also shine or project through the insert to provide light around the sample container 102.

In some embodiments, the sample container holders 110 disposed along the ring 106 may be permanently mounted in the ring 106. For example, as shown in FIGS. 3 and 5A-7B, the sample container holders 110 may be integral with the ring 106 and may be machined from the ring 106 itself. In other embodiments, the sample container holders 110 may be removable from the ring 106 either as a set of several holders or individually and the apparatus 100 may be functional with less than all of the sample container holders 110 of the ring 106 being in place.

The apparatus 100 further comprises a removable lid 114 to allow access to the interior of the apparatus 100 and an interface unit 116 to allow an operator to interact with the apparatus 100. The interface unit 116 may be a combination of a display to output information to the operator and input buttons to receive instructions from the operator. In at least one embodiment, the interface unit 116 may be provided by a touchscreen that the operator may directly touch to provide certain inputs to the apparatus 100.

Figure 9:
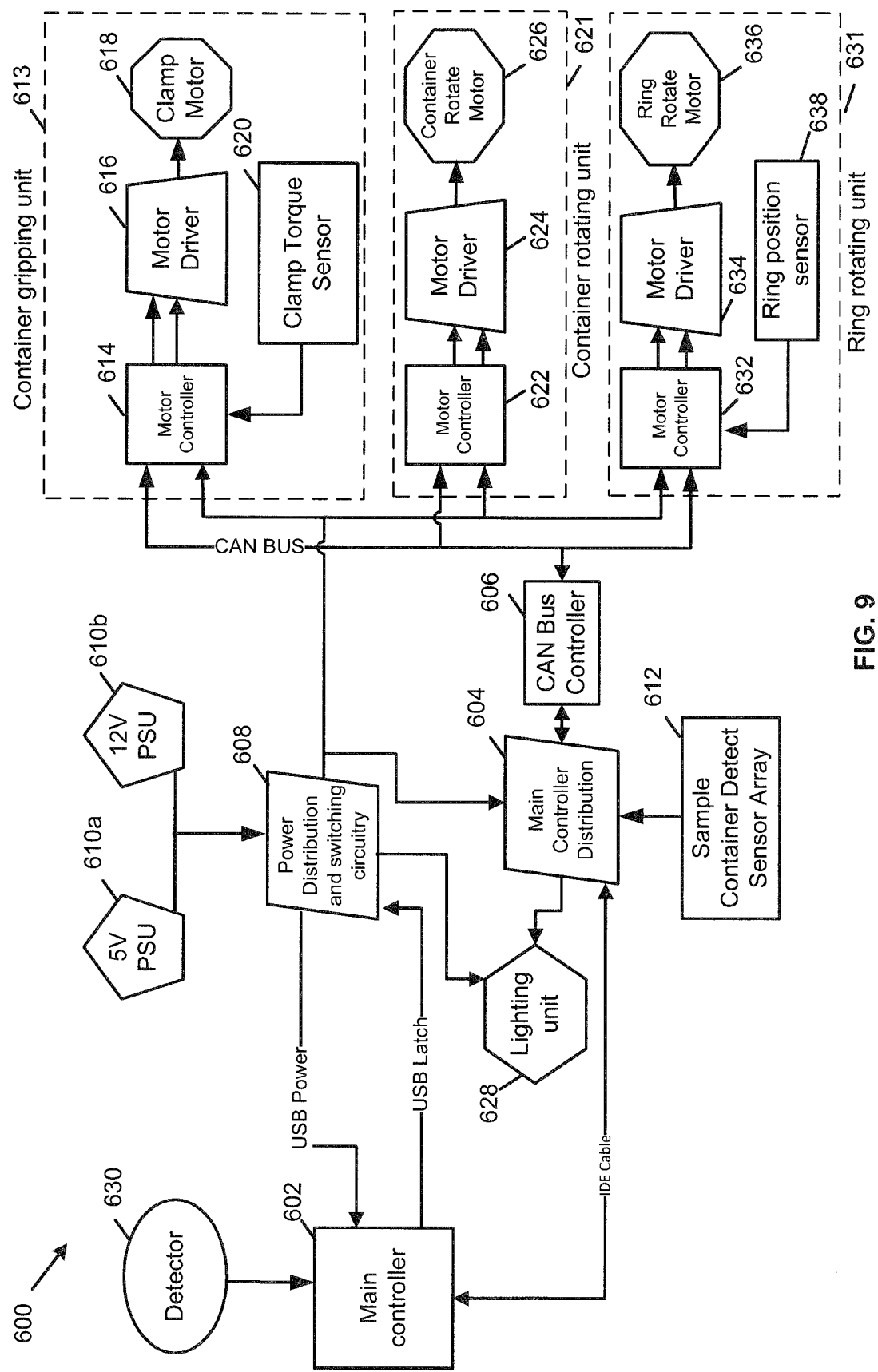
FIG. 9 is a schematic view of an example embodiment of the electrical system that may be used with the apparatus of FIG. 1 or FIG. 3.

It is understood that the apparatus 100 further comprises a processing unit, a memory unit (that includes voltage and non-volatile memory elements described previously), a power unit, and sensors 550a, 550b, 552a and 552b as was described for the apparatus 10 as well as motor controllers and motors that are in electrical communication with each other and the processing unit. The processing unit is also electrically coupled with the detector and the sensors 550a, 550b, 552a and 552b that may be used. These elements may be located at various areas of the base 104b of the housing 104. An example schematic for these elements is shown in FIG. 9. It should be understood that other embodiments are possible for these hardware elements.

In this example embodiment, the detector (not shown) is stationary and during use the ring 106 rotates to bring each sample container into the field of view of the detector. The detector may be a scanner or computer vision hardware that may scan a marker on each sample container 102 in its field of view. The marker may be a barcode or an identification number, for example. For each scanned sample container 102, the detector may produce detection data corresponding to the data obtained from the marker on that sample container 102, and may transmit the detection data to the processing unit for further processing to determine one or more light properties for a light that will be generated to indicate a property of the sample container 102 as was described for the apparatus 10.

Figure 4:
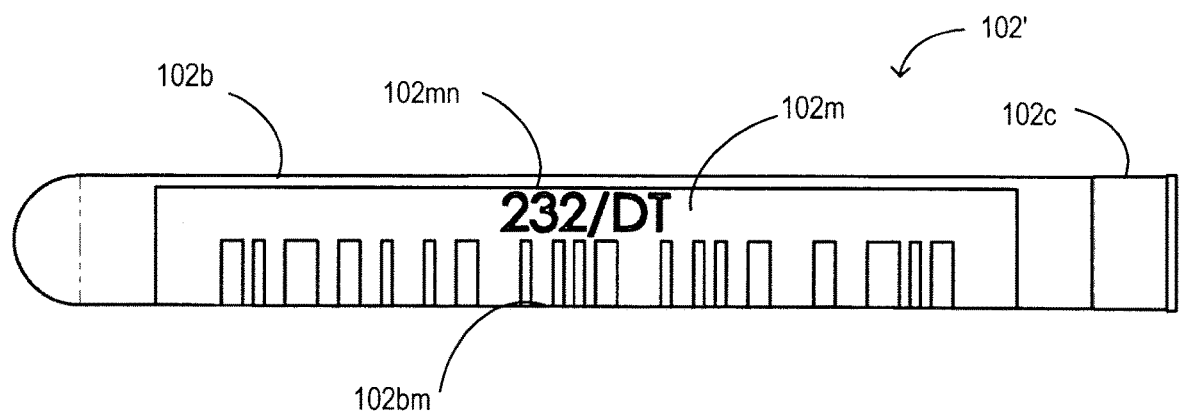
FIG. 4 is an example of a sample container having a marker.

Referring now to FIG. 4, shown therein is an example of a sample container 102'. The sample container 102' is a test tube that comprises a tube body 102b, a cap 102c, and a marker 102m. The marker 102m may include various types of information and may be in various formats. In this example, the marker 102m comprises a bar code 102bm and an ID number 102mn. The ID number 102mn may be optional in cases where the barcode 102bm includes the ID number. Any sample specific information may then be obtained from a database using the ID number. Depending on the particular format for the marker 102m, the detector may be calibrated in order to properly obtain the information that is required to determine one or more properties related to the sample container 102.

Referring again to FIG. 3, during use, the sample container holders 110 in the ring 106 may be loaded with at least one sample container 102 and then processed to determine at least one light property to indicate a particular property related to these loaded sample containers. In this example embodiment, the lighting unit comprises a plurality of groups of light sources that are mounted adjacent to the sample container holders 110 so each group of light sources correspond to one of the sample container holders 110. In other embodiments, one unique light source may be used for each sample container holder 110. The light sources can be seen in FIGS. 5A to 7B and are mounted to the base of the apparatus 100. Accordingly, while the ring 106 rotates, the groups of light sources are stationary and addressable to the closest sample container holder 110. In alternative embodiments, the light sources may be disposed directly on the housing of the apparatus 100, within the ring 106, or mounted within the sample container holders 110.

For example, one property of the sample container 102 may be the name, ID number or location of a laboratory to which the sample container 102 is to be sent, which may be indicated on the marker. In this case, the data obtained by the detector from scanning the marker may be compared with a lookup table or database to determine the one or more light properties of the light that is to be generated by the corresponding light source group. In another example, the information on the marker of the sample container 102 may indicate at least one test that is to be performed on the sample within the sample container 102, and a database that contains destination information for a laboratory that can provide the test can be checked to determine the at least one light property that is associated with the laboratory which is then communicated to the light source for generating the corresponding light. If a sample container 102 has to undergo two different tests it may need to be sent to a special lab for further or more advanced testing.

Accordingly, in this example embodiment, once the sample containers 102 have been processed by the detector by scanning the markers on the sample containers 102, the corresponding groups of light sources can be controlled to emit light with at least one light property that corresponds to which analysis machine or analysis department the sample container 102 is to be sent for further testing (usually there are 3 or 4 of these analysis machines or analysis departments in a hospital lab). In alternative embodiments, other properties of the sample containers 102 may be detected by the detection unit and indicated by using at least one light property including light color, light intensity and/or lighting effects, as described previously for the apparatus 10.

In this example embodiment, there is a plurality of groups of light sources, which are light-emitting diodes. Each of the light-emitting diodes may produce one color in a predefined set of colors when that light-emitting diode is enabled by a light control signal, and each color in the predefined set of colors may correspond to a possible value for a property related to the corresponding sample container, the sample contained therein or an operational status of the apparatus 100. For example, each color in the predefined set of colors may identify a possible property of the sample container 102, which may be further indicated to an operator of the apparatus 100 by consulting a lookup table or a legend. The legend may include a textual description that describes the meaning of each light color (and/or possibly light intensity and/or possibly lighting effect in other embodiments). For example, the legend may state that the color red indicates that a sample in the sample container 102 is past an expiry date, the color green may indicate that the sample container 102 is to be sent to Lab A for a first type of test, and that the color blue may indicate that the sample container 102 is to be sent to Lab B for a second type of test. In some embodiments, there may be repeating sequence of a first color being projected onto and/or around at least a portion of the sample container 102, optionally followed by a brief pause and then a second color being projected onto and/or around at least a portion of the sample container followed by a brief pause which may mean that the sample container is to be sent to a first floor associated with the first color where some operations are to be performed and then a second floor associated with the second color where some other operations are to be performed.

Figure 5A:
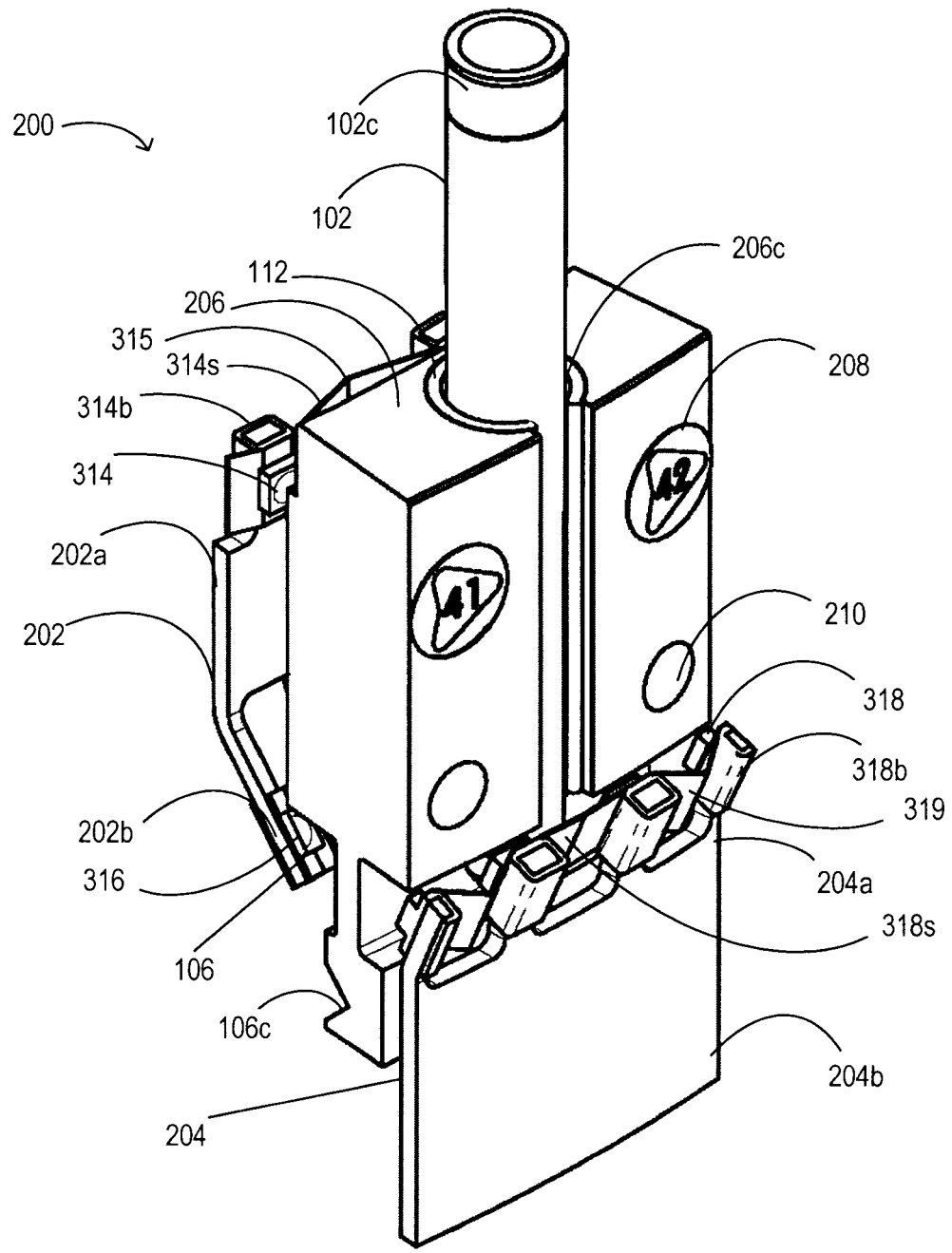
FIG. 5A is an isometric view of an example embodiment of a sample container holder used in the apparatus of FIG. 3.

Referring now to FIG. 5A, shown therein is an isometric view of an example embodiment of a sample container holder 200 provided by a portion of the ring 106 that may be used to hold a sample container 102. The sample container 102 has a cap or lid 102c. The apparatus 100 comprises an inner light source bracket 202 having an upper portion 202a and a lower portion 202b, and an outer light source support bracket 204 having an upper portion 204a and a lower portion 204b. The sample container holder 200 comprises a main body 206 containing the insert 112 and being shaped to define a receptacle or channel 206c, a container holder ID 208, and a light source projection pathway 210. The body 206 of the sample container holder 200 is formed integrally with the ring 106. The support brackets 202 and 204 may have angled portions so that LEDs may be mounted on these angled portions to face a portion of the sample container 102 for illuminating the portion of the sample container 102 when enabled during use since the light produced by the LEDs is generally focused rather than dispersed. The ring 106 may have a groove or channel 106c which may receive another element, such as a bearing for example, to keep the ring 106 properly aligned as it rotates during operation.

Each of the sleeves 112 may be shaped so as to receive and support a sample container 102. The sleeve 112 may be made from different materials that may or may not be compressible and in at least some embodiments these materials may be transparent or translucent. The sleeve 112 may have various shapes to receive and maintain the sample container 102 in a desired orientation. For example, a sleeve 112 may have a uniform or slightly tapered internal diameter that is slightly larger than an outer diameter of at least one type of sample container 102 which the sleeve 112 may be designed to receive. In the embodiment where the diameter of each sleeve 112 is tapered, the tapering may permit for more than one size and type of sample container 102 to be supported within or by the sleeve 112. This may be achieved by making the diameter at a widest portion of each sleeve 112, which may be at or near the top of each sleeve 112, slightly larger than a diameter of a largest sample container in a set of sample containers for which each sleeve 112 may be designed, and by making a diameter at a narrowest portion of each sleeve 112, which may be at or near the bottom of each sleeve 112, slightly smaller than a diameter of a smallest sample container in that set of sample containers. Therefore, the sleeves can be used that have the proper dimensions for the particular sample containers that are used with the apparatus 100. In addition, a lower portion 206b of the receptacle 206c, as shown in FIG. 5B, may have a concave or bowl shape to receive and support a lower portion of the sample container 102 during use.

Figure 5B:
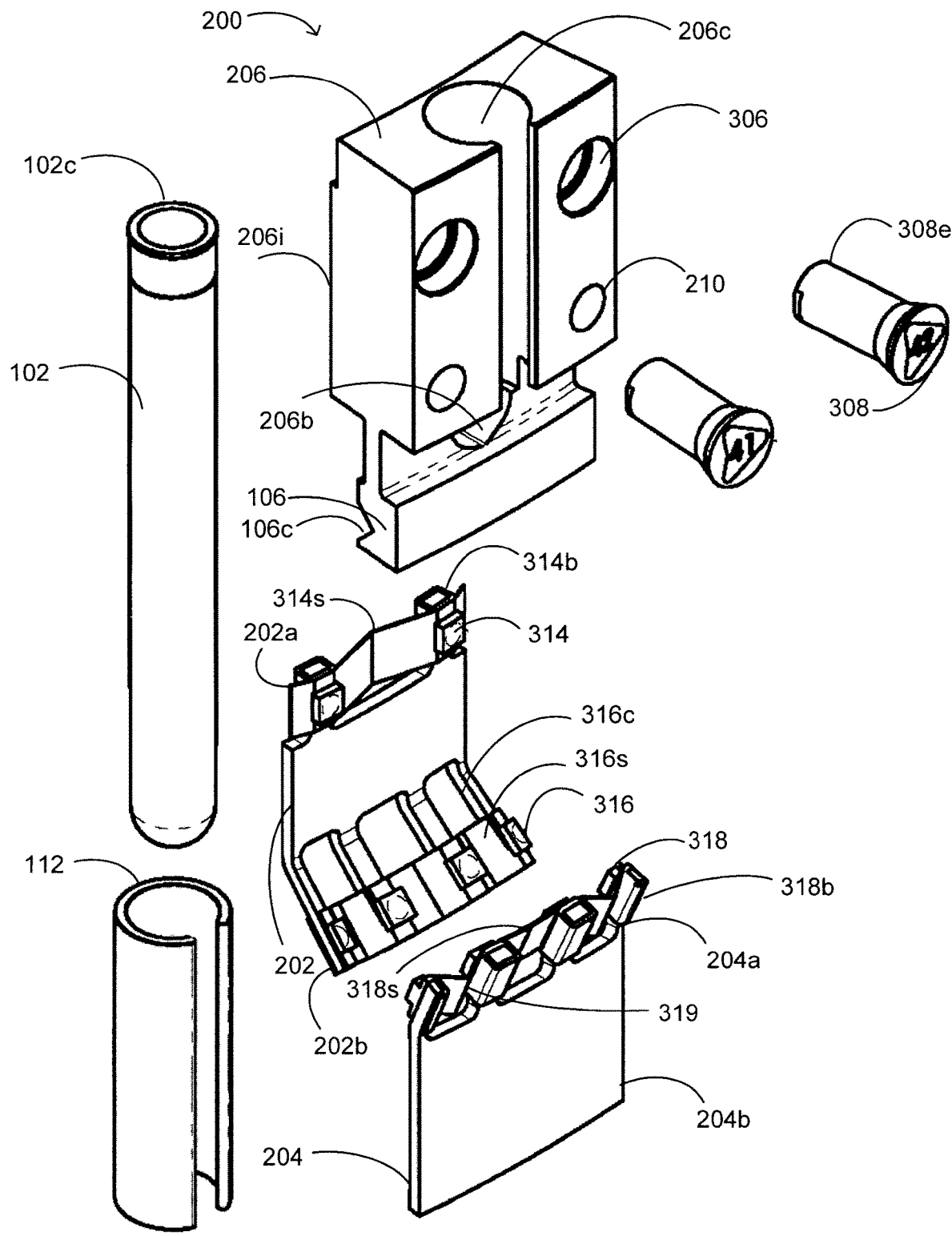
FIG. 5B is an isometric view the sample container holder of FIG. 4 used in the apparatus of FIG. 3 when disassembled.

Referring now to FIGS. 5B to 7B, shown therein are various views of the sample container holder 200 of FIG. 5A. As shown in FIG. 5B, the container holder ID 308 may have a cylindrical shape that fits within channels 306 in the body 206 of the sample container holder 200. The group of light sources for the sample container holder 200 comprises several sets of LEDs including an upper set of inner LEDs 314 that are disposed on the upper portion 202a of the inner light source bracket 202, a lower set of inner LEDs 316 that are disposed on the lower portion 202b of the inner light source bracket 202 and an upper set of LEDs 318 that are disposed on the upper portion 204a of the outer light source support bracket 204. Only one LED from each LED set has been labelled for ease of illustration. Each LED set is generally oriented towards the sample container receptacle 206c. However, there may be other embodiments in which the LEDs may be oriented differently and optical coupling may be used to channel any generated light from the LEDs to the sample container 102. An example sample 102s within the sample container 102 is shown in FIG. 7A.

Figure 7A:
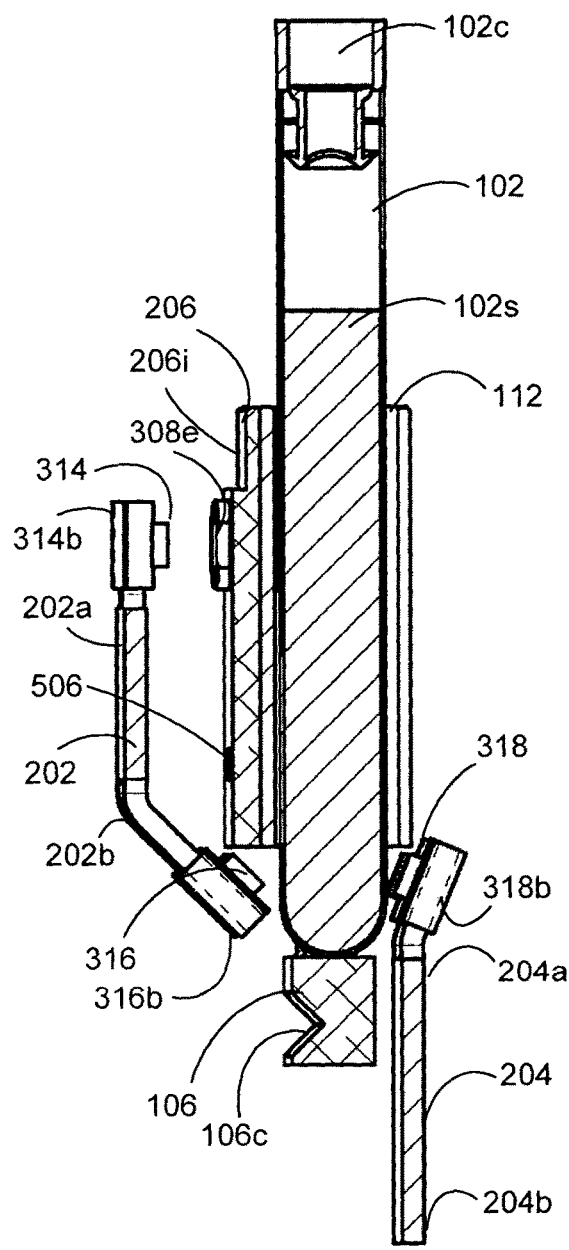
FIG. 7A is a sectional view of the sample container holder of FIG. 4 that is used in the apparatus of FIG. 3, taken along line A-A in FIG. 6A.
Figure 7B:
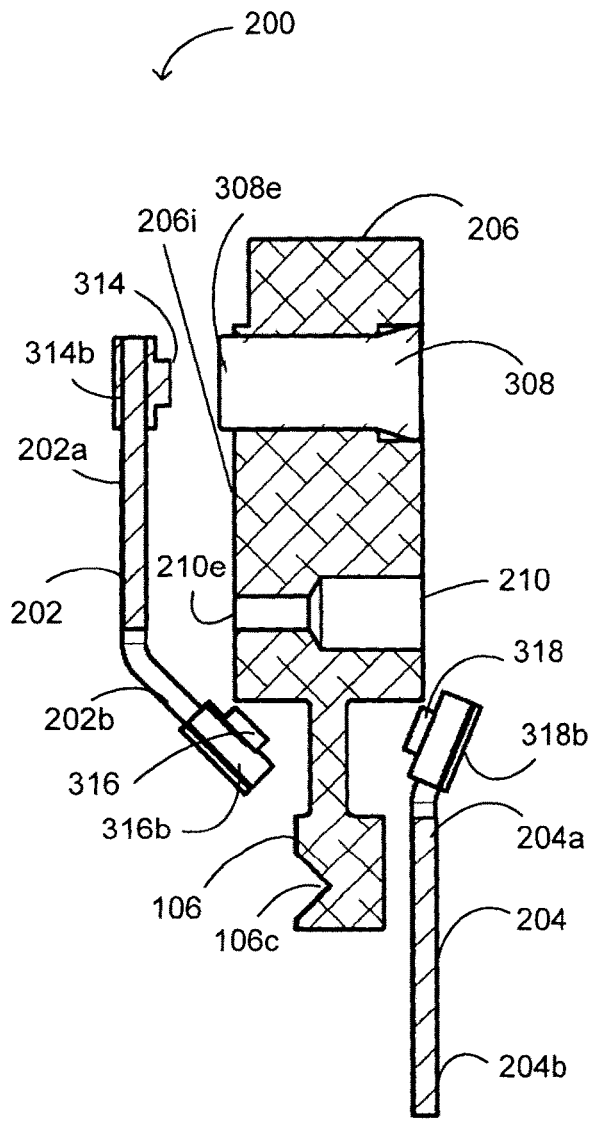
FIG. 7B is a sectional view of the sample container holder of FIG. 4 that is used in the apparatus of FIG. 3, taken along line B-B in FIG. 6A, with the sample container having a sample.

In this example embodiment, the upper set of LEDs 318 of the outer light source support bracket 204 may be directed towards the bottom portion 206b of the receptacle 206 to illuminate a lower portion of the sample container 200 when enabled by the light control signal during use. This light also travels through the sample container 102 and may be optically coupled to the light source projection pathways 210 so that light generated by the LEDs 318 may be channeled towards the front of the sample container holder 200. In at least some embodiments, the light source projection pathways 210 may end in an aperture 210e that is on the inner surface 206i of the body 206 of the sample container holder 200 as shown in FIG. 7B. In some embodiments, the aperture 201e may receive a pin (not shown) that is used to home the ring 106 to its position with respect to a locator pin 506.

In addition, in at least some embodiments, as shown in FIG. 5B, the container holder ID 308 may be made of a translucent or transparent material and may extend to a back inner surface 206i of the sample container holder body 206 that is adjacent to the inner surface of the upper portion 202a of the inner LED support 202. Ends 308e of the container holder ID 308 may be flush with or slightly extend past the inner surface 206i of the sample container holder body 206. Furthermore, the upper LEDs 314 may be oriented to face towards the ends 308e of the container holder IDs 308. Accordingly, when light is generated by the upper LEDs 314, the light is transmitted through the container holder ID cylinders 308 to the front of the sample container holder body 206.

As previously mentioned, in at least some embodiments, the sleeve or insert 112 may also be made of translucent or transparent material so that any light generated by the upper set of LEDs 318 or the lower set of LEDs 316 are transmitted through the sleeve 112 towards the top of the sample container holder 200.

The various LEDs and light pathways of the sample container holder 200 allow an operator of the apparatus 100 to easily see the light produced by the light sources with respect to a given sample container holder 200 so that the operator can see what is being indicated for the characteristic for the sample container 200.

The various sets of LEDs 314, 316 and 318 may be implemented using LED strips where each LED is an RGB LED as described previously with respect to the apparatus 10 (an example of an LED strip that may be used is the Sparkfun LED RGB strip although other LED strips provided by other suppliers may be used such as Aliexpress, for example). The LEDs may be "addressable" meaning that each LED pixel can be controlled individually. However, in other embodiments, the LEDS may not be addressable meaning that each LED in an LED string may be the same color/intensity and either on or off.

Each of the LED sets 314, 316 and 318 are mounted on flexible mini printed circuit boards (PCB) and the LEDs in each LED set are also coupled together using conductive traces between the flexible mini PCBs that are on the strips 314s, 316s and 318s, respectively. There may be multiple pieces of strips 314s that are coupled to one another along the circumference of the apparatus 100 when shorter strips 314s are used to form one long strip. Ends of the long strip are coupled to the processing unit or a bus coupled to the processing unit for communication therewith, as well as to a power supply to receive power. The other strips 316s and 318s may be likewise structured. Other circuitry that may be used for operation of the LEDs 314, 316 and 318, such as capacitors and/or resistors, may be mounted on the mini PCBs or coupled with the conductive traces on the strips 314s, 316s and 318s. Element 316c are members, in this case arms, used to hold the LED strips 314s, 316s and 318s in place.

Each LED set can be given an address, and a position encoder (not shown) may be used with the ring 106 such that when the ring 106 rotates during use, a given position of a given sample container 102 is known as well as the sets of LEDs at the given position so that the LED sets at the given position may be provided with a light control signal that is associated with at least one property of the sample container 102 at the given position. Alternatively, as in this example embodiment, each LED may have a micro-controller on the mini-PCB to allow addressing of each separate LED.

Each of the LED strips 314s, 316s and 318s are mounted to the LED support brackets 202 and 204 which also extend around the circumference of the ring 106. Accordingly, the LED support brackets 202 and 204 may be annular and fixed to the base of the apparatus 100. The LED support brackets 202 and 204 may have posts or protrusions 314b, 316b and 318b upon which portions of the LED strips 314s, 316s and 318s may be mounted using an appropriate fastener such as an epoxy or glue. The LED strips 314s, 316s and 318s may be mounted to the posts 314b, 316b and 318b such that the LED strips 314s, 316s and 318s are flat. However, in other embodiments, such as that shown in FIGS. 5A-6C, the LED strips 314s, 316s and 318s may be mounted to the posts 314b, 316b and 318b such that there are bends 315, 317 and 319 in the LED strips 314s, 316s and 318s, which allows the LEDs on these strips to be placed closer together if there are physical space limitations (this also allows more LEDs to be mounted on a given LED strip).

In some embodiments, the LED strips 314s, 316s and 318s may be mounted to the posts 314b, 316b and 318b such that the LEDs 314, 316 and 318 are on the posts 314b, 316b and 318b. In other embodiments, the LED strips 314s, 316s and 318s may be mounted to the posts 314b, 316b and 318b such that the LEDs 314, 316 and 318 are between adjacent posts 314b, 316b and 318b. In other embodiments, the LED strips 314s, 316s and 318s may be mounted to the posts 314b, 316b and 318b such that the LEDs 314, 316 and 318 are both mounted on and between adjacent posts 314b, 316b and 318b.

In alternative embodiments, only one or two of the LED sets 314, 316 or 318 may be used for a given sample container 102. In alternative embodiments, there may be a different number of LEDs in each LED set 314, 316 or 318. In addition, in other embodiments, for other applications, the positioning and/or orientation of the LED sets 314, 316 or 318 may be varied.

In alternative embodiments, the various LEDs may be sealed using a sealant to protect the LEDs if the operator decides to perform a bleach, chemical or water cleaning (e.g. wipedown, washdown or spraying) of the apparatus 100 or the ring 106 with the sample container holders 200 mounted thereon or of some of the sample container holders 200 individually. For example, a wipedown may be performed with a damp cloth and a 10% bleach solution.

Referring now to FIG. 8, shown therein is a view of sensors 550a, 550b, 552a, and 552b that may be used with the apparatus of FIG. 1 or FIG. 3 to detect capped or uncapped containers 102 having various heights. The sensors 550a and 550b may be used for detecting if the sample container 102 (e.g. test tube) has a cap 102c and if it is short, respectively. The sensors 552 and 552b may be used for detecting if the sample container 102 has a cap 102c and if it is tall, respectively. In this example, the sample container 102 is a taller test tube. The sensors 550a, 550b, 552a and 552b may be photoelectric sensors or other suitable sensors. The sensors 550a and 550b may be mounted to the apparatus using a vertical mount 554, a platform 556 and fasteners 558. Likewise, the sensors 552a and 552b may be mounted to the apparatus 100 using a vertical mount 560, a platform 562 and fasteners 564. The vertical mounts 554 and 560 may be attached to the base of the apparatus 100. It should be noted that the ring 160 is not shown in FIG. 8 for ease of illustration.

Referring now to FIG. 9, shown therein is a schematic view of an example embodiment of an electrical system 600 that may be used with the indication apparatus 10 or 100. The electrical system 600 may be implemented using any suitable controllers, switches, wiring, motors and processors known in the art and a different layout may be used for the electrical system 600 in other embodiments.

The electrical system 600 comprises a main controller 602, main controller distribution 604, a CAN BUS controller 606, power distribution and switching circuitry 608, power supply units 610a and 610b, a sample container detect sensor array 612 (which may also be known as an object detect sensor array), a container gripping unit 613 comprising a motor controller 614, a motor driver 616, a clamp motor 618 and a clamp torque sensor 620, a container rotating unit 621 comprising a motor controller 622, a motor driver 624 and a container rotate motor 626, a lighting unit 628, a detector 630, and a ring rotating unit 631 comprising a motor controller 632, a motor driver 634, a ring rotate motor 636 and a ring position sensor 638. In some embodiments, the ring rotating unit 631 may instead be referred to as an object translation unit which operates to move the object to the detector for processing. The electrical system also includes memory elements (not shown), which may be included as part of one or more of the controllers. In some embodiments, the electrical system 60 may also include components for a recapping unit.

The processing unit of the apparatuses 10 or 100 may be considered to be distributed between the various controllers which have dedicated tasks including the main controller 602, the CAN BUS controller 606, the motor controller 614, the motor controller 622 and the motor controller 632. At least one memory elements is also included (not shown).

The main controller 602 controls the overall operation of the apparatus 100. Accordingly, the main controller 602 may issue control signals to certain hardware elements, such as the lighting unit 628 and the detector 630, or to other controllers which perform specialized operations, such as the motor controllers 614, 622 or 634. The main controller 602 also receives input data from various hardware elements such as the sample container detect sensor array 612 so that the main controller 602 can detect certain operational conditions and can process the sample containers.

The main controller 602 may send control signals and receive sensor data and other data using the main controller distribution 604 and the CAN bus controller 606. The main controller distribution 604 may be a set of wires coupling input and output pins of various components as needed for sending control signal to different components and/or receiving input data or sensor signals from various components. The CAN bus controller controls communication of the main controller 602 with the motor controllers 614 and 622 in a local area network according to the CAN bus standard.

The main controller 602 may be implemented using Raspberry Pi hardware (see https://en.wikipedia.org/wiki/Raspberry_Pi) or other suitable processing hardware. The main controller 602 may use a micro (Secure Digital) SD card (not shown) for memory storage although other memory elements may be included with the main controller 602. In some embodiments, at least one additional memory element, such as an additional SD card, may be used to store one or more databases and settings, so that it can be used in a replacement apparatus if needed. For example, the apparatus that is typically used may be sent for maintenance and/or repairs in which case a replacement apparatus may be used with the SD card from the current apparatus so that the database data and operator settings from the current apparatus passes seamlessly to the replacement apparatus.

The power supply units 610a and 610b are similar to the power unit 20 of the apparatus 10. The power supply units 610a and 610b provide the power needed to operate each of the hardware components of the electrical system 600. In this example embodiment, the power supply units 610a and 610b comprise a 5V power supply and a 12V power supply, respectively, to satisfy the requirements of low power hardware that can run off of a lower power supply (i.e. 5V) and high power hardware that needs a higher power supply for operation (i.e. 12V). Other power supplies of higher or lower voltages may be used in other embodiments.

The power signals provided by the power supply units 610a and 610b may be sent to the various hardware components of the electrical system 600 through the power distribution and switching circuitry 608, which may be implemented using various techniques. For example, Field Effect Transistors (FETs) may be used to switch the positive line of the power distribution circuitry. The FETs can be controlled by switches or microcontrollers (via GPIO pins of the main controller 602.

The sample container detect sensor array 612 may be used to detect various types of sample containers. For example the sample containers may be short or tall and may be capped or uncapped. In this case, the sample container detect sensor array 612 may comprise 4 sensors that each sense whether different sample containers are present as is shown in FIG. 8. For example, when the sample containers are test tubes, the sensor 550*b* may sense whether a short (e.g. 75 mm tall) tube is present, the sensor 550*a* may sense whether a short tube with a cap is present, the sensor 552*b* may sense whether a tall tube (e.g. 100 mm tall) is present and the sensor 552*a* may sense whether a tall tube with a cap is present. This may be done by locating the sensors 550*a*, 550*b*, 552*a*, and 552*b* at different heights so that the top of a given tube is within its field of view. There may be more or less sensors and/or other types of sensors in other embodiments. There may be other sensors that sense other types of sample containers in other embodiments. In at least one embodiment, the sensors in the sample container detect sensor array 612 may be photoelectric sensors (e.g., see http://www.alliedelec.com/pepperl-fuchs-ml100-8-h-350-rt-102-115/70404778/).

The container gripping unit 613 may be used to firmly grasp the sample container so that further actions may be performed such as moving or rotating a given sample container. Accordingly, the container gripping unit 613 has a clamp (not shown) that is actuated by the clamp motor 618 to place the clamp around the given sample container and apply a gripping force to the given sample container. The clamp torque sensor 620 measures the amount of the gripping force to ensure that enough gripping force is applied to so that the clamp firmly holds the given sample container but not too much gripping force is applied as this may result in damage to the given sample container. The amount of grip force applied by the clamp is dictated by the claim motor which receives power supply and control signals from the motor driver 616 which is in turn controlled by the motor controller 614, working in conjunction with the main controller 602.

The container rotating unit 621 may be used to rotate the given sample container when it is gripped by the container gripping unit 613. The given sample container may be rotated so that it can be scanned by the detector 630. Accordingly, the container rotating unit 621 has a container rotate motor 626 that is coupled to the given sample container (not shown) that is being gripped in order to rotate the given sample container by a certain amount. The amount of rotational force provided to the given sample container is dictated by the motor driver 624 which is in turn controlled by the motor controller 622, working in conjunction with the main controller 602. The container rotate motor 626 may be implemented using a stepper motor which can be controlled to move a specific number of steps in order to rotate the sample container by a certain amount.

In other embodiments, the container rotating unit 621 may not be needed where the sample container holder may be implemented so that the sample containers can only be inserted in a certain manner so that it they are facing the proper direction needed for processing by the detector 630 without having to move the sample container.

The ring rotating unit 631 may be used to rotate the ring 106 to bring a given sample container to the detector 630 or to position one or more sample containers at a certain location. For example, the ring 106 may be rotated to position a certain portion of the sample container holders at the front of the apparatus 100. The ring rotating unit 631 has a ring rotate motor 636 that is coupled to the ring 106 (not shown) in order to rotate the ring 106 during use. The amount of rotational force that is provided by the ring rotate motor 636 and the time for which the rotational force is applied is dictated by the ring rotate motor 636 which receives power supply and control signals from the motor driver 634 which is in turn controlled by the motor controller 632, working in conjunction with the main controller 602.

The motor controllers 614, 622 and 634 may be implemented by any suitable motor controller such as Arduino controllers. The motor drivers 616, 624 and 634 may be implemented by any suitable motor drivers such as, but not limited to, Anaheim Automation 2-phase stepper motor drivers, for example. The clamp motor 618, the container rotate motor 626 and the ring rotate motor 636 may be implemented using motors that provide enough gripping and rotational forces, respectively. For example, the motors 618, 626 and 636 may be implemented using any suitable motors such as, but not limited, by 2-phase stepper motors.

The lighting unit 628 generally refers to all of the light sources that are used by the apparatus 100. The light sources may be implemented as described previously for the apparatus 100. In this case, the LED sets that are associated with a given sample container holder receive light control signals from the main controller 602 and power supply signals from the power supply units 610*a* and 610*b* via the power distribution and switching circuitry 608. The circuitry 608 allows a set of LEDs associated with a particular sample container holder to be activated or allows more than one set of LEDs that are collectively associated with more than one sample container to be activated. Furthermore, the circuitry 608 allows at least one of the intensity of the light generated by the LEDs, the color of the LEDs and any lighting effects (as described previously for the apparatus 10) to be selected and implemented.

The implementation of the power distribution and switching circuitry 608 may include using FETs. In other embodiments, relays, or other electronically controlled switching mechanisms/components may be used.

The LED lights may be implemented using suitable LEDs such as those in RGB LED strips as described previously. In this case, each LED may operate on a three wire system with a dedicated light controller that communicates with the main controller 602 to control one or more properties of the generated light such as color, intensity and/or lighting effects. With the RGB LED strips, there may be up to 16 million possible colors, different intensity levels and the different lighting effects may include pulsing, strobing, flashing, or alternating between different colors.

As previously described, the one or more light properties applied to the LEDs can be determined based on various factors, conditions or inputs that are received and/or determined by the main controller 602. For example, the color, intensity or lighting effect of the light generated on or around a sample container can be controlled to occur after a result (or a lack of result) of a whole variety of conditions such as, but not limited to, analytic testing (e.g. weight, level, color, consistency, or more complicated analysis) of the samples or the sample containers, the date/time that the sample container was processed, if the sample container is now ready to be processed, or if the sample container has a new status or destination. Other conditions may include whether the ring 106 is empty or full of sample containers, whether a barcode of a sample container has been successfully scanned and archived, or if a cap is on top of a given sample container that is currently being processed by the apparatus 10 or 100.

The detector 630 may be used to determine a value for a particular property related to the sample container being processed or a sample within the sample container as previously described with respect to the apparatus 10 or the apparatus 100. The detector 630 may be physically disposed in close proximity to the clamp (not shown) that is operated by the container gripping unit 613 and the container rotating unit 621 to detect a property of the sample container when it is oriented in a particular manner. The detector 630 can be implemented by using various means depending on what is to be detected. For example, the detector 630 may be a barcode scanner, a computer vision system, or an RFID reader.

In some embodiments, there may be additional sensors that may be used to provide additional functionality for the apparatus 100. For example, RFID readers (not shown) may be used to determine if any empty rack has been placed beside the apparatus where processed sample containers may be deposited. This may be done for archiving purposes in case an old sample container needs to be pulled. The sample containers that are capped and archived may be indicated by projecting a light on at least a portion of these sample containers where the light has a particular color, such as green, to indicate to the operator that these sample containers are ready to be archived. The operator may place the processed sample containers into the rack beside the apparatus 100 and then place the rack in a refrigeration unit, such as a cooler, when the rack is full. If a sample container needs to be pulled after storage in the refrigeration unit for further testing, the operator may enter the sample container ID into the user interface of the apparatus 100 and the apparatus 100 may display which rack the sample container has been placed into. The operator can now walk into the refrigerator unit, pull the specific rack and quickly locate the sample container. This may significantly reduce the amount of time operators spend searching for particular sample containers.

Figure 10:
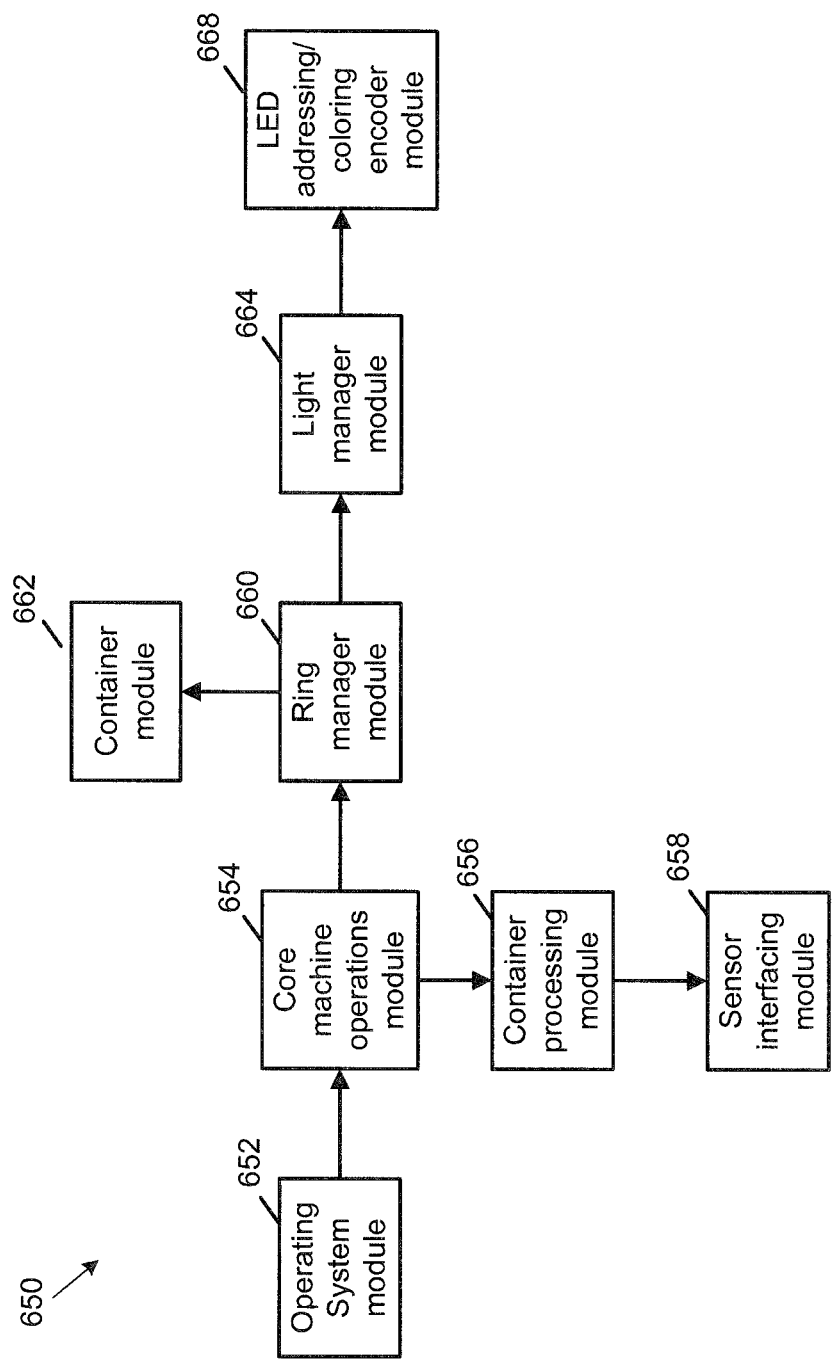
FIG. 10 is a block diagram of an example embodiment of software modules that may be used with the apparatus of FIG. 1 or FIG. 3.

Referring now to FIG. 10, shown therein is a block diagram of an example embodiment of a software system 650 that may be used with the indication apparatus 10 or 100. The software system 650 may comprise an operating system module 652, a core machine operations module 654, a container processing module 656 (also known as an object processing module), a sensor interfacing module 658, a container module 662 (also known as an object module), a ring manager module 660, a light manager module 664, and an LED addressing/coloring encoder module 668. In other embodiments, there may be other modules or some of the modules in FIG. 10 may be combined or further divided into separate modules. The software system 650 may be used in combination with the electrical system 600 to implement the apparatus 100. In some embodiments, a camera may be included for taking pictures of the sample container and/or sample. In some embodiments, there may also be a container capping/recapping module (to be used with known capping/recapping hardware, for example).

The operating system module 652 enables the operation of the various software modules for the apparatus 100, such as the main control program which executes when the apparatus first starts (e.g. boots up), for example.

The core machine operations module 654 controls all of the modules for the apparatus 100. Accordingly, the core machine operations module 654 may also operate to relay data between the various software modules of the software system 650.

The container processing module 656 may be used to obtain and format sample container data such as, but not limited to, at least one of barcode data, sample container size, and cap state (e.g., on or off), for example. The sample container data may be sent to the ring manager module 660. The container module 662 may be used to store sample container data for each sample container holder on the ring 106. The sample container data may also be stored in a database. The container module 662 effectively digitally replicates the physical ring 106 and the objects contained therein. The container module 662 may also be assigned one or more light properties for each object as the system 100 processes the object, and stores the one or more light properties for that object for later access.

The sensor interfacing module 658 may be used to access general purpose input/output (GPIO) devices for the apparatus 100, such as the touchscreen 116 and any input buttons. The sensor interfacing module 658 may also be used to interface with any sensors that may be used by the apparatus 100 in terms of receiving data that is measured by these sensors.

The ring manager module 660 may be used along with the container module 662 to generate light control data needed for generating the light for a given sample container holder (in some cases the light may be generated based on whether there is any missing or invalid information for the given sample container holder). For example, any time the ring 106 is moved or the status of a sample container changes, the system 100 may call the ring manager module 660 to access all the container instances and get the corresponding light property data for the different sample containers. The ring manager module 660 may then merge all the property data for the various sample containers into lighting control data, which is then sent to the light manager module 664.

The ring manager module 660 may also be configured to determine what data is invalid or missing based on what may be expected. For example, every sample container may be defined to have a barcode, so if the container module 662 indicates that a particular sample container does not have a barcode, then the light associated with that particular sample container holder may be assigned a specific color to indicate missing or invalid data. Other examples of missing or invalid information include one or more of:
  there is no sample in the sample container;
  there is no cap on the sample container when there should be;
  a sample container was detected, but the apparatus can't grip it;
  a sample container's height or cap state does not match possible options (indicating sensor failure);
  the sample container does not have a valid destination;
  the barcode/identifier scanned does not match formatting rules; and
  a sample container with the same ID has already been processed.

Otherwise, if the sample container data is considered valid, and assuming other requirements are met, then the ring manager module 660 may determine the light color, light intensity (optional) and/or lighting effects (optional) that are to be used depending on the particular property and/or value for the particular property that is to be indicated for the given sample container. The ring manager module 660 then sends the light control data to the light manager module 664.

The light manager module 664 may be used to manage the lighting functions by translating the ring's sample container data and/or status data, as the case may be, into light control data for the LED encoder 668. An LED or set of LEDs may continue to emit light with the assigned one or more light properties for a given sample container until it's told to emit a different light or different light property. This may be extended to multiple LEDs/multiple sets of LEDs for multiple sample container holders that may be lit at the same time using the same or different lighting properties.

The LED addressing/coloring encoder module 668 encodes the light control data that is received from the light manager module 664 for being sent to a particular group of LED sets. This may be determined from position data provided by the ring position sensor 638. The light control data is sent to the appropriate hardware (e.g. the power distribution and switching circuitry 608) and the lighting unit 628 for generating the sample container holder lights during operation.

The apparatus 100 may be used when sample containers first arrive at a lab. For example, when a lab technician receives a group of blood samples, they need to know what the current status is of the samples and/or what the destination is for the samples. Conventionally, they must manually enter the ID # or scan the barcode of each sample container into the lab system which will then display the sample information via text. After reading this sample information, the lab technician can then decide the best way to perform the tests and separate the sample containers into different racks for sending the sample containers to the appropriate destination as well as noting any special notes. This manual method has a much higher risk of incurring human errors such as sending sample containers to the wrong destinations, which may lead to the wrong test being performed but more importantly delay the proper test being done thus increasing the time between when the sample is obtained and when the medical professionals are able to receive the results of the ordered test, interpret the results and take appropriate action if needed.

In contrast, with at least one of the apparatus and methods taught in accordance with the teachings herein, the operator (i.e. lab technician) may load a group of sample containers into the ring 106 and select a sort function via the user interface 116. The operator may then leave the apparatus alone as it indexes through each sample container, detecting the sample container ID, loading sample container data about the sample container from the lab database, determining the at least one light property associated with the given sample holder and generate and project the light towards at least a portion of the sample container where the light is based on the at least one light property. The operator may then come back to the apparatus to find the lights projected on the different sample container holders to be lit up in one of N predefined colors, where N is an integer. For example, there may be 4 distinct colors and any sample containers that receive a projected light having first light color may be sent to a first destination for further handling, any sample containers that receive a projected light having a second light color may be sent to a second destination, any sample containers receiving a projected light having a third light color may be sent to a third destination, and any sample containers receiving a projected light having a fourth light color may have an issue that requires further attention or manual processing by the lab operator. At this point the operator can unload all of the sample containers by color and send them off to their corresponding destinations.

In at least some embodiments, the apparatus may index each sample container by moving the sample container to the detector 600, clamping the sample container, rotating the sample container, scanning the marker of the sample container as it is being rotated and comparing the scanned information with the lab system to find out which test needs to be performed. If the sample container was not found in the lab information system then the sample container data may be automatically entered by the apparatus into the lab information system. Using this sample container data, the apparatus can indicate via at least one light property the status or destination of each individual sample container.

Other checks may also be performed by the apparatus such as, but not limited to, determining if the samples need to be centrifuged, determining if a given sample container needs to be uncapped, and determining the next destination for the given sample container. Different light colors may be used to indicate this information. For example, sample containers that have samples needing to be centrifuged may be indicated and illuminated by blue colored lights, sample containers needing to go to a chemistry analyzer may be indicated and illuminated by green colored lights, and sample containers needing to go to a hematology analyzer may be indicated and illuminated by purple colored lights. If a sample container needs attention or special testing it may be indicated and illuminated using an orange colored light or if there was an issue that needed immediate attention such as insufficient sample volume or an unreadable barcode then these sample containers may be indicated and illuminated using red colored lights.

Staff can use the apparatus described herein to quickly sort and separate the sample containers into different racks destined for different analyzers or labs. This offers a massive time savings as well as reduces the chances of sample containers being sent to the wrong destination which may delay the test results being sent to the doctor. Without the lighting, in accordance with the teachings herein, the staff may have to pick up each sample container individually and scan the barcode or enter the 9 or 10 digit sample container ID number into the system, which is prone to error.

In at least one embodiment, when a sample container is indexed into the processing area (also known as an interrogation zone) of the apparatus and is successfully scanned into the system, several operations may be performed. For example, at the processing area, a detector can detect the presence of a sample container, a clamping arm can clamp the sample container, spin the sample container, scan the sample container for identification on the sample container and detect the presence of a cap on the sample container, for example. If the apparatus includes a recapper then a cap can be inserted onto the sample container if deemed necessary. The upper portion of the sample container and/or cap may be photographed before being removed from the processing area and assigned to a rack. Various sample container data may be stored in the database such as, but not limited to:
- sample container ID (e.g. barcode);
- Date and/or Time which may be the time that the sample was collected or an internal date/time stamp from when the sample was first processed by the apparatus;
- Capped (yes/no);
- If the sample container is capped, then a camera (not shown) may take an image of the cap; and
- a rack ID number for the rack that the sample container has been assigned to (in an example embodiment, the apparatus comprises RFID technology (not shown) to detect the ID number of the rack that is currently pressed up against the apparatus for unloading).

Once the apparatus has processed enough sample containers to fill the rack full of sample containers, then the operator may place the full rack in an assigned location, which may be within a refrigeration unit, for example. Any of the aforementioned information may be utilized further down the line for a number of reasons such as, but not limited to, sample container recovery, and rack rotation.

In sample container recovery, after a medical practitioner, such as a doctor, views the results of a test on a sample, the doctor may wish to have the sample tested again or have a different test performed. This currently involves a technician going into the refrigeration unit to find the sample by manually looking through each rack and checking the barcode ID number on each sample container. This is a time consuming job. For example, a technician may sometimes spend up to or over 2 hours trying to recover a single sample container.

However, when using an apparatus and processing methodology in accordance with the teachings herein, the technician can go to the apparatus, enter the sample container ID number and instruct the apparatus to check its database and return: 1) the date/time of sample container processing, 2) the image of the cap (if taken) so the physical search for the container can also be narrowed down by color (assume in this example the cap is blue), and 3) the rack ID number. The technician can then go into the refrigeration unit, locate the rack with the corresponding rack ID number and check all the sample containers with blue caps on them to locate the desired sample container. This process may now take up to about 5 minutes instead of up to about 2 hours.

In rack rotation, since the samples in the sample containers may "spoil" after about a week or so, labs are typically in the process of discarding sample containers with old samples while adding sample containers with new samples. Each lab may have their own internal rules for how long to keep a sample, which is generally set due to the capacity of the refrigeration unit and/or racks and the replacement threshold may be in the range of about 3-7 days. Therefore, it is not usual for racks from different days to be kept in different areas of the refrigeration unit but this sometimes results in mix-ups, or samples being kept too long or samples being thrown out by mistake while still being valid.

However, when using an apparatus and processing methodology in accordance with the teachings herein, when the technician does their daily clear out of old samples, they can set a value X for how long they wish to keep the sample containers and run a cleanup cycle on the apparatus in which the main processing unit will search the database for old sample containers and deliver a list of the racks that have the sample containers that are over X days old relative to the data/time data described previously. The technician can then go to the refrigeration unit, pull those racks on the list and dump the old sample containers in the list. This greatly reduces the possibility of a sample container being discarded too soon or sample containers with old samples that are no longer good taking up valuable space in the rack and refrigeration unit.

In at least one example embodiment, a method for identifying sample containers using the apparatus 10 or the apparatus 100 may comprise performing an initialization sequence on the apparatus; indicating that the apparatus is ready to receive sample containers; indexing one of the sample containers for analysis; determining a value for a property of the sample container, a characteristic of the sample within the sample container or an operational characteristic of the apparatus itself; generating a light control signal defining one or more light properties based on the determined property where the light properties include a light color, optionally a light intensity and optionally lighting effects; and projecting a light onto at least a portion of the sample container where the light has the determined light properties. If there are one or more sample containers still to be analyzed, then the indexing, determining, generating and displaying acts may be repeated for the one or more sample containers.

Figure 11:
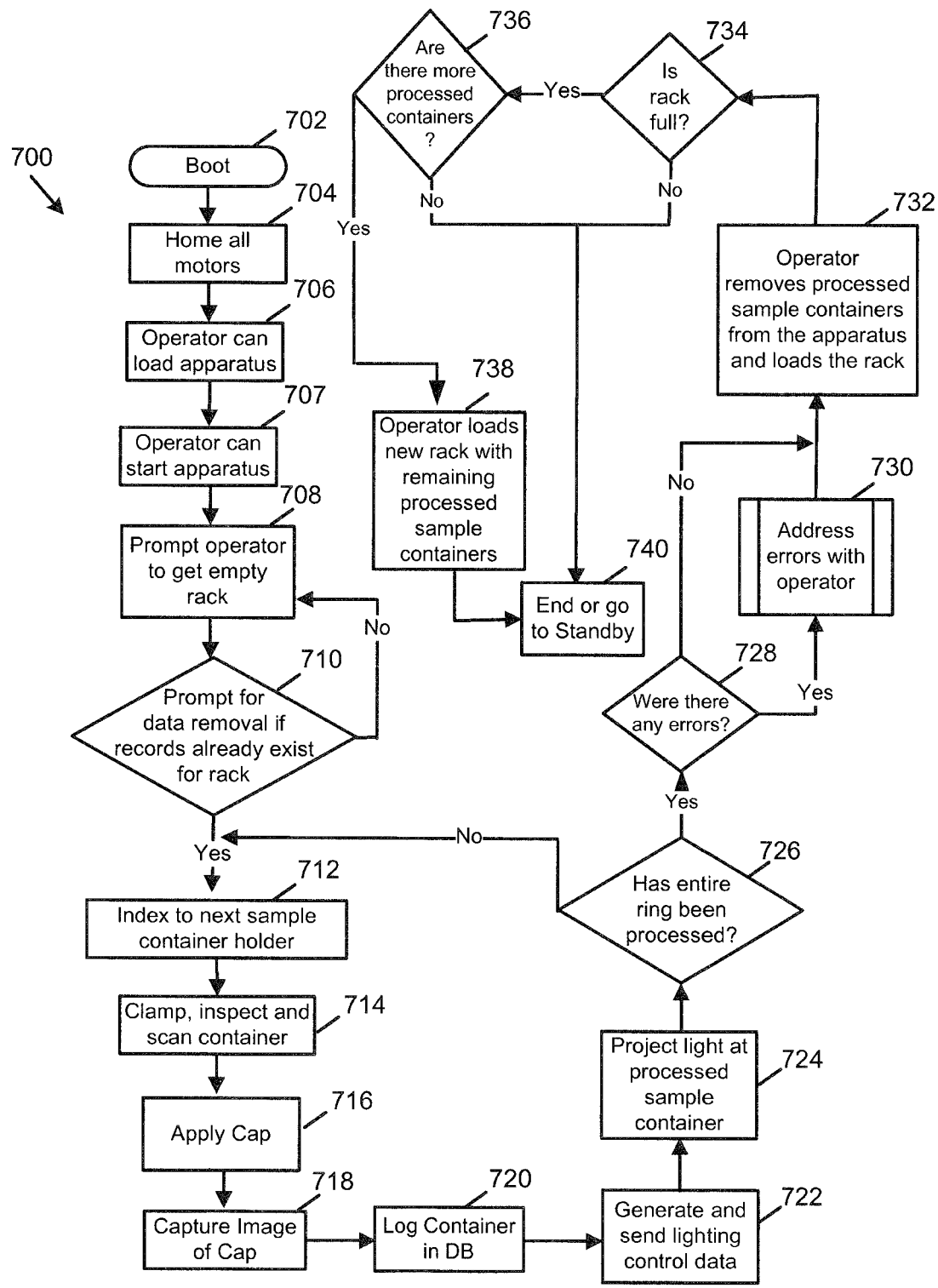
FIG. 11 is a flowchart of an example embodiment of a method for indicating a property of an object using the apparatus of FIG. 3.

Referring now to FIG. 11, shown therein is a flowchart of an example embodiment of a method 700 for indicating a property of a sample container using the apparatus 100. The method 700 assumes that the apparatus 100 is first turned on and the ring 106 is empty. It should be noted that for method 700 the operator can be a human or a robot. Also, in alternative embodiments the apparatus may be oriented so that the sample container holders are arranged linearly instead of as a ring but for ease of description, the apparatus in method 700 is described as having the sample container holders oriented in a ring.

At act 702, the apparatus 100 boots up and starts to run through its initialization procedure so that it is ready for operation. This may involve performing various self-tests to make sure that various sensors, motors and moving parts are working and initializing various variables. This may also involve configuring the motors and their associated actuators to be at their respective home positions at act 704. This initialization act may also involve testing the lighting unit and generating lights at the various light sources.

At act 706 the operator can start loading the apparatus with sample containers that require processing (e.g. sorting) if desired. This may be done until all of the sample container holders are full. In some embodiments, the sample containers may have just come from an analyzer and may need to be uncapped.

At act 707, once the sample containers have been loaded, the operator can then start the apparatus 100 to being processing the sample containers that have been loaded onto the apparatus. For example, the operator can push a start button, the user interface 116 (e.g. the operator may press a start icon on the touch screen) or some other input on the apparatus to instruct the apparatus to start processing sample containers.

Alternatively, in some embodiments, the operator may not load the apparatus 100 and may instruct the apparatus 100 to commence operation.

At act 708, the operator is prompted to obtain an empty rack that can be placed adjacent to (e.g. on either side of the apparatus 100), in proximity to (e.g. beside or above) or placed a bit farther away from the apparatus 100 and data regarding the rack is obtained. For example, if the apparatus 100 includes an RFID reader and the rack has an RFID tag, then the operator can push the rack up to the RFID reader so that the apparatus 100 can read the rack id and the capacity of the rack (i.e. the quantity of sample containers that it can hold). The prompt may be provided by a visual message via the user interface 116 (i.e. display) or possibly via an audio message in some embodiments. In some embodiments, the empty sample container holders on the ring may be illuminated by a light having a certain color, e.g. the color blue, and/or other light property like flashing, to indicate they are ready to be loaded with fresh sample containers for processing. Alternatively, in other embodiments, if the apparatus 100 does not have any rack sensors, or if these sensors are not operational, then the operator may enter the rack ID # into the apparatus 100 using the user interface 116.

At act 710 if older records for this current rack exist in the database then the operator may be prompted to remove the older records in order to start storing records for the current sample containers from the current rack as these containers are processed.

At act 712, the ring is rotated so that a sample container requiring processing may be brought into the processing and inspecting position (near the detector) where it may be processed by the detector 630. During processing, the apparatus 100 indexes through each sample container holder on the ring 106 one at a time.

At act 714, in some embodiments, at the processing position, the sample container may then be clamped and rotated so that a marker, or other feature, of the sample container may be detected by the detector 630. In some embodiments, the clamping and rotating may not be needed if the sample container holder is designed so that the operator places the sample container in the sample container holder in such a way that it can always be properly processed by the detector 630 without having to be rotated. Once processed, the ring 106 may be rotated to bring the next sample container holder to the processing area.

In some embodiments, act 714 may also include inspecting the sample container which can include determining if the sample container is a short (e.g. 75 mm) or a tall (e.g. 100 mm) sample container. This detection may be done by the detector 630 or by using separate dedicated sensors as previously described. The height of the sample container may be needed to determine if the sample container has a cap on it or not and needs to be capped. In some embodiments, if there is no cap present, then the apparatus 100 may have a capping unit that can place a cap on the sample container by isolating a cap, orienting it properly and then pressing the cap onto or into the sample container. Accordingly, when a cap is needed, the apparatus 100 needs to know if the sample container is tall or short so that it can properly place the cap on the sample container (e.g. determine how far to vertically push the cap on the sample container). At this point, the sensors or the detector 630 may do another check to confirm that the sample container has been successfully capped or recapped. If this is not done properly then a light may be displayed to indicate an error and the error may be registered/flagged for further inspection/processing.

Accordingly, act 714 results in detection data being obtained for the current sample container being processed. Act 714 may also optionally include receiving input data (as described previously for apparatus 10) where the input data is related to the sample container being processed in order to determine the at least one property of the sample container. A detection signal is generated containing the detection data and optionally the input data.

At act 716, the method 700 determines whether a cap is needed for the sample container and applies a cap when needed using a capping unit as explained previously (a conventional capping unit may be used as is known to those skilled in the art). In some cases, sample containers with caps on them may be loaded into the apparatus 100 so that the apparatus can process them for archival purposes. In alternative embodiments, this act may not be performed (e.g. if there is no capping unit).

At act 718, the method 700 may include using a camera of the apparatus 100 to obtain an image of the cap of the current sample container that is being processed for reasons explained previously. In other embodiments, the image may also include the sample container itself. For example, an image of the top portion of the sample container and cap may be obtained.

At act 720, the method 700 may include automatically logging the current sample container being processed into a database using the sample container information that was detected by the detector 630 and for which sample container information data was generated. The sample container information may contain various data items as described previously such as, but not limited to, date, time, specimen id #, the image from act 718, the ID # of the current rack that the sample container will be placed into after processing, test information about at least one test scheduled for the sample container, a destination for the sample container, and an expiry date after which the sample container will need to be discarded, for example. It should be noted that in some embodiments, logging at least some of the data into the database may be optional; for example, data logging may not be needed if the location/status of the samples does not need to be recalled/accessed at a later time.

At act 722, the method 700 then generates and sends light control data to the light source(s) that correspond to the sample container holder that is being processed. As previously discussed, the light control data includes at least one light property such as a light color, a light intensity and/or lighting effects depending on the particular implementation. The light control data may be determined by reading a portion of the detection data or the input data obtained from performing detection on the object, by: 1) comparing a portion of the detection data or the input data to one or more thresholds, 2) using logic rules on a portion of the detection data or the input data, 3) using a portion of the detection data or input data as an index into a database or 4) obtaining time and/or date information in the detection data or the input data or 5) using the time and/or date of when the detection was performed or the input data was obtained. For example, the light control data may be determined directly from a portion of the sample container information data or by using a portion of the sample container information data to access a database record which will specify a value for the particular properties to be identified for the sample container and one or more associated light properties (e.g. light color, optionally light intensity and optionally lighting effects) or by using logic rules and comparing at least a portion of the sample container information data to one or more thresholds or conditions. At act 724, the light source(s) located at the sample container holder that has just been processed display a light according to the light control signal.

At act 726, the method 700 determines if all of the sample container holders in the ring 106 that have sample containers have been processed. If this is not true, then the method 700 proceeds to act 712 at which point the next sample container holder is indexed for processing and acts 714 to 724 are repeated.

If the determination at act 726 is true, then the method 700 proceeds to act 728 where the method 700 determines whether there were any errors in processing any of the sample containers. If this is true then the errors are identified to the operator at act 730 so that they can be addressed by the operator. This may include using particular light properties such as light colors to indicate certain types of errors for the sample containers that encountered errors. A visual prompt and/or audio prompt may also be provided to the operator through the user interface of the apparatus.

For example, in at least one embodiment, the color red may be used to indicate that a sample container needs attention, which may, for example, be due to a marker not being affixed correctly or not being affixed at all on the sample container or being unscannable thus making it not possible to detect any sample container information at the detector. The operator may view more information about the error on the user interface and address the issue before sending the sample container through the apparatus 100 again for processing.

In some embodiments this may also include rotating the ring 106 of the apparatus 100 so that the sample containers requiring attention are positioned at a particular location. In some embodiments, the errors may be prioritized and the sample containers with the highest priority errors may be positioned for further handling by the operator by rotating the ring 106 to a particular position. In some embodiments, once a sample container with an error has been handled by the operator, the ring 106 may be rotated to position the sample container having the next highest priority error to a certain location for further handling by the operator to deal with the error.

If the determination at act 728 is not true or after the errors have been addressed by the operator, the method moves to act 732 where the operator removes the processed sample containers from the apparatus 100 and loads the current rack with them. The operator may know to do this action based on visual information that is displayed to the operator via the user interface, using certain light properties with lights that illuminate or project all of the sample container holders that require unloading, and providing audio information to the operator via the user interface. For example, the color green may be used to indicate that a sample container has been successfully scanned and recapped (if this recapping function is provided). Alternatively, other colors may be used to indicate different destinations.

In some embodiments, the apparatus 100 may indicate only the sample containers that need to be unloaded based on the space available in the current rack. For example, if there are 40 processed sample containers in the ring of the apparatus 100 and there is only room for 30 processed sample containers in the current rack then the apparatus will project a particular light (e.g. green) onto and/or around at least a portion of 30 sample containers, while the remaining 10 sample containers may not have a projected light or may have a projected light that is a different color to indicate that they are to be unloaded into the next rack.

At act 734, the apparatus 100 determines if the current rack is full. This may be done by prompting the operator to input data on whether all of the processed sample containers have been successfully unloaded from the apparatus and loaded into the current rack (obtained at act 708). In some embodiments, this may be done by comparing a count of successfully processed sample containers to the storage capacity of the current rack. Once capacity for the current rack has been reached, the apparatus 100 may prompt the operator to load/assign a new rack before it will instruct for any sample containers to be unloaded.

If the current rack is full the method 700 proceeds to act 736 at which point it is determined if there are more processed sample containers that have to be unloaded. If this determination is true, then the method 700 proceeds to act 738 where the operator obtains a new rack with space for processed sample containers. In some embodiments, once a new rack has been obtained, the apparatus can project a different light onto and/or around at least a portion of the processed sample containers that need to be unloaded to indicate that they can now be unloaded. After all of these processed sample containers have been unloaded the method 700 proceeds to act 740.

If at act 734 it is determined that the current rack is not full, then the method 700 proceeds to act 740. All of the sample container holders can be illuminated with a particular color indicating to the operator that new sample containers requiring processing can now be loaded. The apparatus 100 can then remain in standby mode or it may be powered off.

Once the operator is ready to process more sample containers, the method 700 can proceed to act 706 where the operator can load the apparatus with the new sample containers and start the apparatus at act 707 and the rest of the method 700 is re-executed.

In other embodiments, the apparatus 10 or the apparatus 100 can be modified so that a display or instrumentation panel (if included) can have electronics that provides backlighting. During operation the backlight color of the display and/or instrumentation panel can be changed to have a particular light property (i.e. one or more of a particular light color, a particular light intensity, and a particular lighting effect) to indicate that a particular problem has occurred.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

The invention claimed is:

1. A method of indicating at least one property related to an object, the method comprising:
   detecting the at least one property related to the object or receiving input data for the at least one property related to the object using a detector and generating a detection signal including the detection data and/or the input data;
   determining at least one light property that corresponds to the at least one property related the object based on the detection signal using a processing unit;
   producing a light control signal having a light property that is based on the determined at least one property related to the object; and
   generating and projecting a light having the light property, after the detection, onto the object to illuminate and/or encompass at least a portion of the object with the light and to indicate the at least one property related to the object, where the light property is based on the light control signal.

2. The method of claim 1, wherein the object comprises one of a container, a solid, a gas, a liquid, a sample, a sample within a container, a surface of an item and a body of an item.

3. The method of claim 1, wherein the property related to the object comprises one or more of a status of the object, a destination of the object, a physical property of the object, a chemical property of the object, a time property of the object, a quantitative property of the object, a qualitative property of the object, a test status for the object, or a status of an apparatus that is performing the method.

4. The method of claim 1, wherein the method comprises generating the light to have a certain color to indicate the at least one property related to the object.

5. The method of claim 1, wherein the method comprises generating the light to have a constant intensity or to have a varying intensity by pulsing the light, strobing the light, flashing the light or sequentially varying the light according to a predetermined pattern to indicate the at least one property related to the object.

6. The method of claim 1, wherein the method comprises generating the light electrically, atomically, biologically, chemically and/or percussively.

7. The method of claim 1, wherein the method comprises generating the light adjacent to the object or remotely from the object.

8. The method of claim 7, wherein the method comprises generating the light to shine directly towards the object or projecting the generated light towards the object by using optical coupling.

9. The method of claim 1, wherein the method comprises determining the at least one light property by reading a portion of the detection data or the input data obtained from performing detection on the object, by comparing a portion of the detection data or the input data to one or more thresholds, by using logic rules on a portion of the detection data or the input data, by using a portion of the detection data or input data as an index into a database or by obtaining at least one of time and date information in at least one of the detection data and the input data or by using at least one of the time and date of at least one of when the detection was performed and the input data was obtained.

10. The method of claim 9, wherein the object includes a marker having object information and the method comprises detecting the marker to include the object information in the detection data, and using a portion of the object information for the at least one property related to the object or using the portion of the object information to search a database for the at least one property related to the object.

11. The method of claim 10, wherein the object information comprises tests to be performed on the object, and/or a destination for the object as the at least one property related to the object.

12. The method of claim 1, wherein the method comprises moving the object linearly or rotationally to the detector for detection or moving the detector linearly or rotationally to the object for detection, wherein the movement of the object or the detector is along a one dimensional axis, a two dimensional or a three dimensional axis including a vertical or horizontal axis.

13. The method of claim 1, wherein the method comprises generating the light with a first color to indicate that the object has successfully undergone the detection act and generating the light with a second color to indicate that there has been an error in performing the detection act on the object.

14. The method of claim 1, wherein the object is one of a biological sample, an oil sample, a gas sample, a soil sample, a solid sample, a liquid sample, a mineral sample and food and the detection comprises testing the object for a condition and generating the light to indicate that the object has passed or failed the condition.

15. The method of claim 14, wherein the method comprises using at least one of a different light color, a different light intensity or a different lighting effect to indicate a severity of the test result.

16. An apparatus for determining and indicating at least one property related to an object, the apparatus comprising:
- a detector that is configured to generate detection data or receive input data for the at least one property related to the object and generate a detection signal including the detection data and/or the input data;
- a lighting unit including at least one light source, the lighting unit being configured to receive a light control signal, generate a light having a light property determined based on the detection signal and project the light to illuminate and/or surround at least a portion of the object to display the at least one property related to the object;
- a memory unit that comprises software code for data acquisition and lighting control; and
- a processing unit that is operatively coupled to the detector, the lighting unit and the memory unit, wherein the processing unit is configured to execute the software code to first receive and analyze the detection signal for determining the at least one property related to the object and secondly generate and send the light control signal having the light property to the light unit.

17. The apparatus of claim 16, wherein the object comprises one of a container, a solid, a gas, a liquid, a sample, a sample within a container, a surface of an item and a body of an item.

18. The apparatus of claim 16, wherein the property related to the object comprises one or more of a status of the object, a destination of the object, a physical property of the object, a chemical property of the object, a time property of the object, a quantitative property of the object, a qualitative property of the object, a test status for the object, or a status of the apparatus.

19. The apparatus of claim 16, wherein the lighting unit is configured to generate the light to have a certain color to indicate the at least one property related to the object.

20. The apparatus of claim 16, wherein the lighting unit is configured to generate the light to have a constant intensity or to have a varying intensity by pulsing the light, strobing the light, flashing the light or sequentially varying the light according to a predetermined pattern to indicate the at least one property related to the object.

21. The apparatus of claim 16, wherein the lighting unit is configured to generate the light electrically, atomically, biologically, chemically and/or percussively.

22. The apparatus of claim 16, wherein the at least one light source is adjacent to or remotely disposed from the object and is oriented to project the generated light towards and/or around the object.

23. The apparatus of claim 16, wherein the at least one light source is adjacent to or remotely disposed from the object, and the apparatus includes at least one optical coupler to project the generated light towards and/or around the object.

24. The apparatus of claim 16, wherein the processing unit is configured to determine the at least one property related to the object by reading a portion of the detection data or the input data in the detection signal, by comparing a portion of the detection data or the input data to one or more thresholds, by using logic rules on a portion of the detection data or the input data, by using a portion of the detection data or input data as an index into a database or by obtaining at least one of time and date information in at least one of the detection data and the input data or by using at least one of the time and date of at least one of when the detection was performed and input information was obtained.

25. The apparatus of claim 24, wherein the object includes a marker having object information, the detector is configured to detect the marker and include the object information in the detection data, and the processing unit is configured to use a portion of the object information for the at least one property related to the object or to use the portion of the object information to search a database for the at least one property related to the object.

26. The apparatus of claim 24, wherein the object information comprises tests to be performed on the object, and/or a destination for the object as the at least one property related to the object.

27. The apparatus of claim 16, wherein the apparatus comprises one or more actuators move the object linearly or rotationally to the detector for detection or to move the detector linearly or rotationally to the object for performing detection, wherein the movement of the object or the detector is along a one dimensional axis, a two dimensional or a three dimensional axis including a vertical or horizontal axis.

28. The apparatus of claim 16, wherein the apparatus is stationary and the object is located in close proximity to the detector for detection.

29. The apparatus of claim 16, wherein the lighting unit is configured to generate the light with a first color to indicate that the object has successfully undergone detection and to generate the light with a second color to indicate that there has been an error in performing detection on the object.

30. The apparatus of claim 16, wherein the object is one of a biological sample, an oil sample, a gas sample, a soil sample, a solid sample, a liquid sample, a mineral sample and food, the detector is configured to test the object for a condition and the at least one light source is configured to generate the light to indicate that the object has passed or failed testing for the condition.

31. The apparatus of claim 30, wherein the lighting unit is configured to generate the light with at least one of a different light color, a different light intensity or a different lighting effect to indicate a severity of the test result.

32. The apparatus of claim 16, wherein the apparatus further comprises a housing and at least one object holder coupled to the housing for holding at least one object.

33. The apparatus of claim 32, wherein the apparatus comprises a ring that is rotatably mounted to the housing, the ring comprising a plurality of object holders, and the lighting unit comprising a plurality of light sources mounted adjacent to the object holders, mounted to the housing or mounted to a base portion of the apparatus, where each light source is addressable to a given object.

34. The apparatus of claim 33, wherein the apparatus comprises a ring rotating unit having a motor that is coupled to the ring and configured to rotate the ring is to bring a given object holder having a given object adjacent to the detector for determining the at least one property for the given object.

35. The apparatus of claim 16, wherein the object is a sample container and the apparatus comprises an object holder having a receptacle with an insert for receiving the sample container, the insert being transparent or translucent and the generated light is optically coupled to the insert for illuminating the object.

36. An apparatus for determining and indicating at least one property related for each object of a plurality of objects, the apparatus comprising:
a plurality of object holders for holding the plurality of objects;
a detector that is configured to generate detection data or receive input data for the at least one property related to each of the objects and generate a detection signal including the detection data and/or the input data for each of the objects;
a lighting unit that comprises a power distribution switching circuitry and a plurality of light sources, the power distribution and switching circuitry being coupled to the plurality of light sources to configure the plurality of light sources to be addressable to a corresponding object holder, receive one of a plurality of light control signals, and generate and project a light to illuminate and/or surround at least a portion of one of the objects to display the at least one property related to the corresponding object where the light has a light property determined based on the detection signal for the corresponding object and encoded in the light control signal;
a memory unit that comprises software code for data acquisition and lighting control; and
a processing unit that is operatively coupled to the detector, the lighting unit and the memory unit, wherein the processing unit is configured to execute the software code to instruct the detector to perform detection and generate the detection signal for each of the objects, receive and analyze the detection signal for determining the at least one property related to each object and generate and send the light control signal having the light property to the lighting unit.

* * * * *

UNITED STATES PATENT AND TRADEMARK OFFICE
CERTIFICATE OF CORRECTION

| | |
|---|---|
| PATENT NO. | : 11,079,401 B2 |
| APPLICATION NO. | : 16/083019 |
| DATED | : August 3, 2021 |
| INVENTOR(S) | : Stephen James Wright et al. |

It is certified that error appears in the above-identified patent and that said Letters Patent is hereby corrected as shown below:

In the Specification

Column 5, Line 13, "...configured to detection a marker..." should read -- configured to detect a marker --.

Column 17, Line 45, "...processes both of this data..." should read -- processes both of these data --.

Column 26, Line 34, "sending control signal to..." should read -- sending control signals to --.

In the Claims

Claim 9, Column 39, Line 12, "...at least one light property..." should read -- at least one property --.

Claim 27, Column 41, Line 6, "...actuators move..." should read -- actuators to move --.

Signed and Sealed this
Twentieth Day of June, 2023

Katherine Kelly Vidal
*Director of the United States Patent and Trademark Office*